US009011840B2

(12) United States Patent
Bartholomew et al.

(10) Patent No.: US 9,011,840 B2
(45) Date of Patent: Apr. 21, 2015

(54) ACTIVATED MESENCHYMAL STEM CELLS FOR WOUND HEALING AND IMPAIRED TISSUE REGENERATION

(75) Inventors: Amelia Bartholomew, Lake Forest, IL (US); Simon Lee, Chicago, IL (US); Erzsebet Szilagyi, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/483,910

(22) Filed: May 30, 2012

(65) Prior Publication Data
US 2013/0017175 A1   Jan. 17, 2013

Related U.S. Application Data

(63) Continuation-in-part of application No. 12/922,417, filed as application No. PCT/US2009/037299 on Mar. 16, 2009.

(60) Provisional application No. 61/565,318, filed on Nov. 30, 2011, provisional application No. 61/587,903, filed on Jan. 18, 2012, provisional application No. 61/036,808, filed on Mar. 14, 2008, provisional application No. 61/049,249, filed on Apr. 30, 2008.

(51) Int. Cl.
*A01N 63/00* (2006.01)
*C12N 5/00* (2006.01)
*C12N 5/02* (2006.01)
*C12N 5/0775* (2010.01)
*A61K 35/28* (2006.01)

(52) U.S. Cl.
CPC .............. *C12N 5/0663* (2013.01); *A61K 35/28* (2013.01); *C12N 2501/24* (2013.01)

(58) Field of Classification Search
None
See application file for complete search history.

(56) References Cited

U.S. PATENT DOCUMENTS

| | | | |
|---|---|---|---|
| 5,607,915 A | 3/1997 | Patton | |
| 6,355,239 B1 | 3/2002 | Bruder et al. | |
| 6,797,269 B2 | 9/2004 | Mosca et al. | |
| 6,875,430 B2 * | 4/2005 | McIntosh et al. | 424/93.7 |
| 7,635,477 B2 | 12/2009 | Scadden et al. | |
| 2005/0169887 A1 | 8/2005 | Shachar et al. | |
| 2005/0197296 A1 | 9/2005 | Tamura et al. | |
| 2005/0239897 A1 | 10/2005 | Pittenger et al. | |
| 2006/0251619 A1 | 11/2006 | Borrelly et al. | |
| 2007/0044163 A1 | 2/2007 | Fagan et al. | |
| 2009/0022684 A1 | 1/2009 | Morley | |
| 2009/0202479 A1 | 8/2009 | Shi et al. | |
| 2011/0002738 A1 | 1/2011 | Mahler et al. | |
| 2011/0020291 A1 | 1/2011 | Banerjee et al. | |
| 2011/0311496 A1 | 12/2011 | Pittenger et al. | |

FOREIGN PATENT DOCUMENTS

| | | |
|---|---|---|
| WO | 2006/052991 | 5/2006 |
| WO | 2007/133580 | 11/2007 |
| WO | 2010/039872 | 4/2010 |

OTHER PUBLICATIONS

Romieu-Mourez "Regulation of MHC Class II Expression and Antigen Processing in Murine and Human Mesenchymal Stromal Cells by INF-gamma, TGF-beta, and Cell Density" Journal of Immunology 2007; 179: 1549-1558.*
Murray et al. "In Vitro and in Vivo Activation of Human Mononuclear Phagocytes by Interferon Gamma" Journal of Immunology 1987, vol. 138, No. 8, pp. 2457-2462.*
Acute Radiation Syndrome (a Fact Sheet for Physicians) p. 1-5 (1992).*
Uccelli et al. "Mini-Review Immunoregulatory function of mesenchymal stem cells" European Journal of Immunology 2006. 36 2566-2573.*
McFarlin et al. "Bone marrow-derived mesenchymal stromal cells accelerate wound healing in the rat" Wound Rep Reg (2006) 14 471-478.*
Krampera et al. "Role for Interferon-gamma in the Immunomodulatory Activity of Human Bone Marrow Mesenchymal Stem Cell" Stem Cells 2006; 24:386-398.*
Lazarus et al., "Cotransplantation of HLA-Identical Sibling Culture-Expanded Mesenchymal Stem Cells and Hematopoietic Stem Cells in Hematologic Malignancy Patients," *Biology of Blood and Marrow Transplantation*, 11:389-398 (2005).
Le Blanc et al., "HLA Expression and Immunologic Properties of Differentiated and Undifferentiated Mesenchymal Stem Cells," *Experimental Hematology*, 31:890-896 (2003).
Le Blanc et al., "Treatment of Severe Acute Graft-Versus-Host Disease with Third Party Haploidentical Mesenchymal Stem Cells," *The Lancet*, 363:1439-1441 (2004).
Murray et al., "In Vitro and in Vivo Activation of Human Mononuclear Phagocytes by Interferon-gamma," *J. Immunol.*, 138(8):2457-2462 (1987).

(Continued)

*Primary Examiner* — Blaine Lankford
*Assistant Examiner* — Thomas J Visone
(74) *Attorney, Agent, or Firm* — Barnes & Thornburg LLP; Alice O. Martin

(57) ABSTRACT

Inflammatory cytokines e.g. IFN-γ, serve as initiating stimuli for mesenchymal stem cell (MSC) immunosuppresive activity in vivo. Other inflammatory cytokines, such as TNF alpha, the molecule hemoxygenase I, and TLR ligation of MSC, may also provide such a response. Activated MSC's promote tissue regeneration in conditions such as aging, where regeneration is impaired. Wound healing in aged mammals was enhanced by restoring tensile strength to the levels of younger mammals. Activated MSCs were useful in treating wounds in diabetic primates.

11 Claims, 21 Drawing Sheets

(56) References Cited

OTHER PUBLICATIONS

Ringdén et al., "Mesenchymal Stem Cells for Treatment of Therapy-Resistant Graft-Versus-Host Disease," *Transplantation*, 81:1390-1397 (2006).
Tang et al., "Down Regulation of MHC II in Mesenchymal Stem Cells at High IFN-gamma can be partly Explained by Cytoplasmic Retention of CIITA," *J. Immunol.*, 180(3):1826-33 (2008).
Acute Radiation Syndrome (A Fact Sheet for Physicians), p. 1-5 (1992).
Holling et al., "Function and Regulation of MHC Class II Molecules in T-Lymphocytes: of Mice and Men," *Hum. Immunol.*, 65: 282-290 (2004).
Kang et al., "A paradoxical role for IFN-$\gamma$, in the immune properties of mesenchymal stem cells during viral challenge," *Experimental Hematology*, 33: 796-803 (2005).
Krampera et al., "Role for Interferon-$\gamma$ in the Immunomodulatory Activity of Human Bone Marrow Mesenchymal Stem Cells," *Stem Cells*, 24: 386-398 (2006).
Murphy et al., "Differential Effects of the Absence of Interferon-$\gamma$ and IL-4 in Acute Graft-Versus-Host Disease after Allogeneic Bone Marrow Transplantation in Mice," *The Journal of Clinical Investigation*, 102(9): (1998).
Newman et al., "Treatment of Inflammatory Diseases with Mesenchymal Stem Cells," *Inflammation & Allergy—Drug Targets*, 8: 110-123 (2009).
Polchert et al., "IFN-• activation of mesenchymal stem cells for treatment and prevention of graft versus host disease," *Eur. J. Immunol.*, 38:1745-1755 (2008).
Ren et al., "Mesenchymal Stem Cell-Mediated Immunosuppression Occurs via Concerted Action of Chemokines and Nitric Oxide," *Cell Stem Cell*, 2: 141-150 (2008).
Rifas, "T-Cell Cytokine Induction of BMP-2 Regulates Human Mesenchymal Stromal Cell Differentiation and Mineralization," *J. Cell. Biochem.*, 98:706-714 (2006).
Rixon et al., "Increased survival of rats irradiated with x-rays and treated with parathyroid extract," *Nature*, 182(4646): 1374 (1958).
Romieu-Mourez et al., "Regulation of MHC Class II Expression and Antigen Processing in Murine and Human Mesenchymal Stromal Cells by IFN-$\gamma$, TGF-$\beta$, and Cell Density," *Journal of Immunology*, 179(3): 1549-1558 (2007).
Ryan et al., "Interferon-$\gamma$ does not break, but promotes the immunosuppressive capacity of adult human mesenchymal stem cells," *Clinical and Experimental Immunology*, 149: 353-363 (2007).
Sun et al., "Pathophysiology of acute graft-versus-host disease: recent advances," *Translational Research*, 150(4): 197-214 (2007).
Wall et al., "The role of tumor necrosis factor and interferon gamma in graft-versus-host disease and related immunodeficiency," *Transplantation*, 57(2): 273-279 (1994).
Whitfield et al., "Parathyroid hormone: A novel tool for treating bone marrow depletion in cancer patients caused by chemotherapeutic drugs and ionizing radiation," *Cancer Letters*, 244(1): 8-15 (2006).
Stagg et al., "Interferon-gamma-stimulated marrow stromal cells: a new type of nonhematopoietic antigen-presenting cell," *Blood*, 107(16): 2570-2577 (Mar. 15, 2006).
Dominici et al., "Minimal criteria for defining multipotent mesenchymal stromal cells. The International Society for Cellular Therapy position statement," *Cytotherapy*, 8(4): 315-317 (2006).
Chan et al., "MHC expression kinetics and immunogenicity of mesenchymal stromal cells after short-term IFN-gamma challenge," *Experimental Hematology*, 36: 1545-1555 (2008).

\* cited by examiner

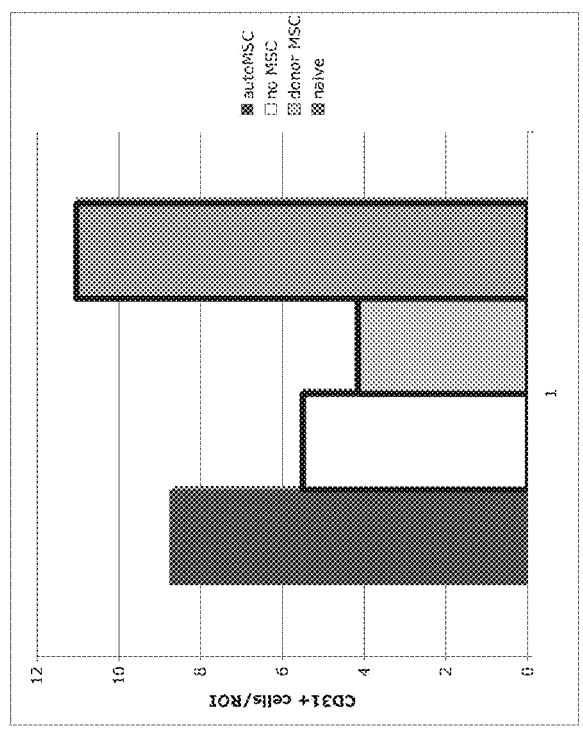
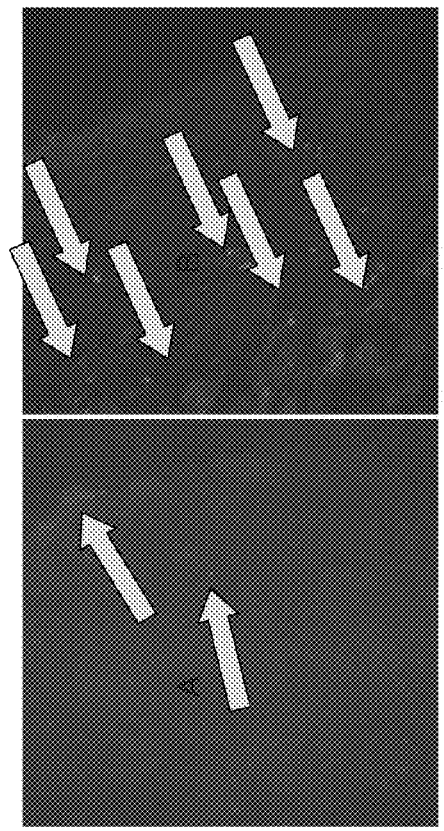
FIG. 9B
FIG. 9A

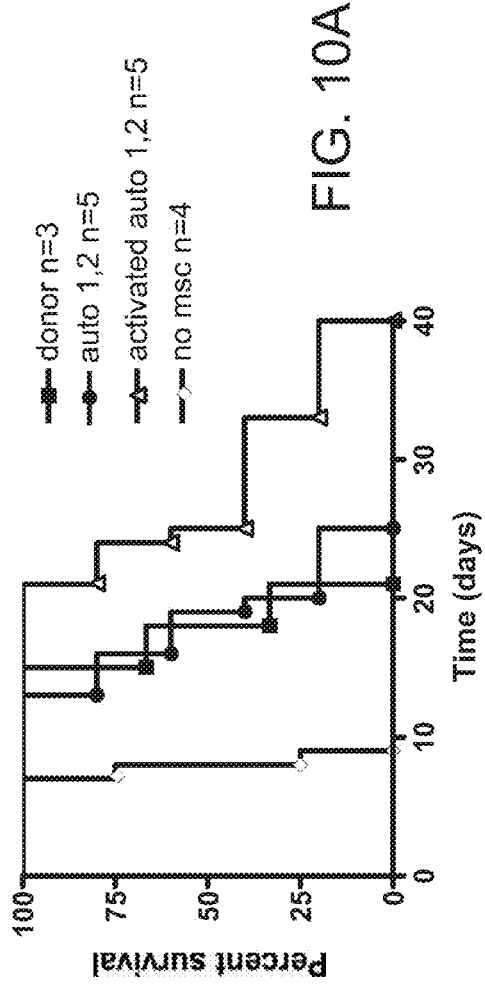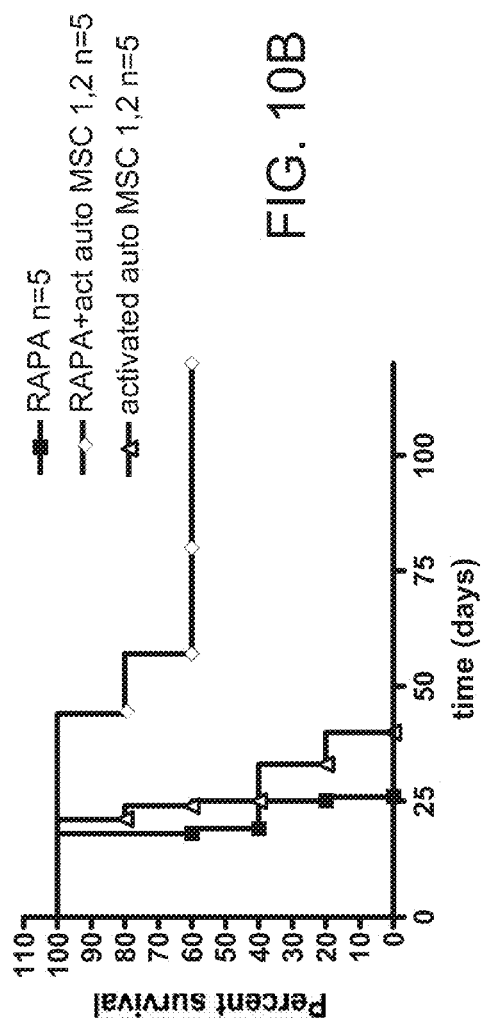

ACTIVATED MESENCHYMAL STEM CELLS FOR WOUND HEALING AND IMPAIRED TISSUE REGENERATION

CROSS REFERENCE TO RELATED APPLICATIONS

This patent application is a continuation-in-part of co-pending U.S. application Ser. No. 12/922,417, filed Nov. 9, 2010 which is a U.S. nationalization under 35 U.S.C. §371 of International Application No. PCT/US2009/037299, filed Mar. 16, 2009, which claims the benefit of priority under 35 U.S.C. §119(e) to U.S. Provisional Application No. 61/049,249, filed Apr. 30, 2008 and U.S. Provisional Application No. 61/036,808, filed Mar. 14, 2008. This application also claims the benefit of priority of U.S. Provisional Application No. 61/565,318, filed Nov. 30, 2011, and U.S. Provisional Application No. 61/587,903, filed Jan. 18, 2012. The disclosures set forth in the referenced applications are incorporated herein by reference in their entireties, including all information as originally submitted to the United States Patent and Trademark Office.

This invention was made with U.S. government support under Grant No. RO1 A1067506 awarded by NIH and Grant No. H8810 awarded by IRMI and Grant No. E6614 awarded by NIH. The U.S. government has certain rights in the invention.

BACKGROUND

Inflammatory cytokines e.g. IFN-γ, serve as initiating stimuli for mesenchymal stem cell (MSC) immunosuppresive activity in vivo. Other inflammatory cytokines, such as TNF alpha, the molecule hemoxygenase I, and TLR ligation of MSC, may also provide such a response. Activated MSC's promote tissue regeneration in conditions such as aging, where regeneration is impaired. Wound healing in aged mammals is enhanced by restoring tensile strength to the levels of younger mammals. Activated MSCs were useful in treating wounds in diabetic primates.

Wound Healing

1. General

With increasing numbers of aging patients undergoing surgery, post-surgical wound care presents obstacles of delayed healing, increased wound infection, and a greater incidence of dehiscence. In the absence of surgery, chronic wounds observed in patients 60 years old or older have increased recurrence, duration, number of wounds and frequency of infection when compared to younger patients. Taken together, these findings indicate an emerging and growing problem in wound care.

The desirable effects of mesenchymal stem cells administered in wounds can be, in part, attributed to their ability to reduce inflammation and enhance regeneration through the recruitment of alternatively activated macrophages, and endothelial cells, and enhanced vascularity. Interestingly, patients of advanced age appear to have diminished capacities in macrophage function with altered production of cytokines, growth factors, expression of TLR, and signaling via the ERK-MAPK pathway. Because macrophages play a significant role in the initial phases of the inflammatory wound response and the subsequent growth phase response by secreting angiogenic growth factors, enhancing macrophage function could facilitate resolution of the impaired wound healing responses observed in the aged. Because wounds of individuals advanced in age suffer from the ability to adequately and thoroughly heal, more potent interferon gamma activated MSC may facilitate wound healing, restoring the tensile strength of the wounds of aged mammals to strengths more commonly observed in young mammals. Bone marrow derived mesenchymal stem cells, activated by interferon gamma, promoted wound tensile strength in wounds of aged mice and monkeys. This effect was due to the subsequent participation of host macrophages.

2. In Diabetic Patients

Diabetes is one of the most frequent causes of compromised wound healing. As a global health concern, the number of diabetic patients worldwide is projected to increase from 197 million reported in 2003 to 366 million by the year 2030. In the United States, the estimated cost of diabetes in 2007 was 174 billion dollars, 58 billion of which was spent on diabetes-related complications.

Chronic wounds in diabetic patients fail to heal due to diabetic macro- and microvasculopathy, macrophage dysfunction and reduced ability of the release and the migration of BM derived and tissue residing pluripotent adult stem cells that can conduct the coordination of the local healing process. Moreover, the low microvascular perfusion inhibits appropriate epidermal and endothelial cell migration of angiogenesis and reepithelisation.

Effective strategies like vascular bypasses and/or epidermal replacement (Apligraf or skin allografts) increase wound healing and closure rates. Even though they also secrete angiogenesis promoting cytokines (vascular endothelial growth factor (VEGF), epidermal growth factors (EGF), platelet-derived growth factor (PDGF), transforming growth factors (TGFs), interleukin (IL)-1α (which is chemotactic for keratinocytes and enhances collagen synthesis), and tumor necrosis factor-α (which enhances fibroblast transformation)) they still do not repair the complex microvascular dysfunction and altered macrophage functions.

New clinical strategies such as the dermal matrix scaffolds, stem cell therapies and local growth hormone replacements are aiming to restore sufficient blood supply and cytokine microenvironment in early inflammatory phase of the healing process to define a more regenerative pattern. Bioengineered matrix scaffolds appears to offer a more complete therapy to reach functionally and anatomically complete healing.

Integra, an FDA approved acellular dermal skin substitute build by extracellular matrix (collagen and GAG), has been reported as successful in the treatment of wide tissue defects or nonhealing wounds like venous leg ulcers.

Locally or systematically administered MSCs have demonstrated improvement in healing, angiogenesis, and collagen content in wounds through producing paracrine factors to recruit macrophages and endothelial cells for tissue regeneration.

MSCs in response to inflammatory environment and signaling (IFN-gamma, TNF-alpha, IL-1beta) increase their effect to inhibit T-cell 1, NK-cell B-cell activation through enhanced production of indoleamine 2.3-dioxygenase, Cox-2, and PGE-2

Graft V. Host Disease

Recent evidence suggests MSC interactions with macrophages reduce pro-inflammatory activity to an anti-inflammatory, pro-regenerative enterprise with increased capabilities to phagocytose apoptotic cells. Such MSC-mediated effects could be due to both cell-cell contact as well as release of paracrine factors. Production of growth factors and cytokines by MSC can be enhanced when MSC are exposed to inflammatory signaling from interferon gamma or tumor necrosis factor. Increased MSC potency, a consequence of ex vivo exposure to interferon gamma, has been demonstrated to powerfully prevent graft versus host disease when comparably, non-interferon gamma activated MSC had no effect.

Graft versus host disease, mediated by donor T cells, is a significant source of morbidity and mortality following allogeneic stem cell transplantation. Mesenchymal stem cells (MSC) can successfully treat ongoing graft versus host disease, presumably due to their ability to suppress donor T cell proliferation. However, little is known about the mechanisms which MSC exert in vivo to prevent graft versus host disease which limits predictions of conditions for optimal effects.

Allogeneic hematopoietic stem cell transplants have the potential to play a significant curative role in the treatment of malignant and non-malignant hematopoietic disorders, autoimmune diseases, immunological deficiencies, and in the induction of transplantation tolerance. Unfortunately, widespread application of this therapeutic modality is limited due to the morbidity and mortality of graft versus host disease (GVHD), which affects 50% of stem cell transplant recipients. Although grafts highly matched to the recipient, young donors, donor/recipient sex match, and post-transplant immunosuppression are strategies used to reduce the risk of GVHD, thus far, the greatest preventative measure has been intentional underutilization of stem cell transplantation. Theoretically, strategies aimed in preventing GVHD would target early initiating factors either during the inflammatory milieu created in the wake of tissue damage from conditioning regimens, or during T cell antigen recognition and proliferation. After the efferent effector phase occurs, donor T cell mediated destruction of host tissues occurs and preventive strategies are replaced with treatment regimens.

Mesenchymal stem cells (MSC) have been used in the efferent phase of GVHD to treat ongoing, acute, steroid resistant GVHD. In contrast, when given at the time of bone marrow transplant, for the prevention of GVHD, the incidence of grade III/IV GVHD was not significantly improved. MSC reliably suppressed large scale T cell proliferation in response to polyclonal stimulation in vitro. In contrast, with allogeneic mixed lymphocyte cultures of variable stimulation, MSC suppression is also variable; MSC do not completely abrogate lymphocyte proliferative responses between all donor and recipient pairs. In addition, MSC do not suppress the modest T cell proliferative response to recall antigens.

Murine experimental models used to dissect the mechanism of MSC effects in the course of GVHD have yielded mixed results, with some studies showing MSC efficacy and others finding no effect. Several factors are likely to contribute to the variable results. MSC tissue source, (i.e., bone marrow, cord blood, adipose tissue), method of isolation to remove myeloid precursors (several weeks vs. rapid immunodepletion) and timing of MSC administration are potential variables which could explain these differences. Notably, such variation has not been observed clinically, with MSC treatment of ongoing GVHD reported to have significant efficacy, while MSC prevention of GVHD not shown to be effective clinically.

SUMMARY

Wound healing is impaired in aged mammals. Mesenchymal stem cells (MSC) exert some beneficial effects in wounds, however promoting healing in the challenging setting of aged skin requires additional potency. MSC enhances production of pro-regenerative cytokines and growth factors when activated with an inflammatory cytokine, for example, interferon gamma. Increased potency of activated MSC facilitates wound healing in aged tissues.

For example, in older mice, tensile strength of healing wounds was significantly lower than in younger animals. Older mice treated with activated MSC showed significant increases in tensile strength, restoring the strength to that observed in young mice.

This effect was dependent on host macrophage activity. Macrophage depletion abrogated the beneficial effect of MSC. Because macrophage function is impaired in aged animals, activated MSC may restore macrophage function in aged animals to that of young animals. These results support the development of activated MSC therapies for enhanced tissue regeneration, especially for older population groups of mammals.

Activated mesenchymal stem cells and Integra scaffold synergised to ameliorate early perfusion and angiogenesis of diabetic wounds in a preclinical non-human primate model.

The beneficial effects of Integra scaffold are combined with interferon activated MSCs to promote early angiogenesis and regenerative microenvironment in diabetic wounds in the early inflammatory phase of the wound healing process. Although MSC's migrate into damaged tissues, their dynamic trafficking and tissue homing when systemically infused or locally injected can not be predicted precisely for effective dose calculations. Local delivery of MSCs through Integra scaffold better supports the need of continuous local microenvironmental effect of MSCs than local injection or systemic administration. The MSC loaded scaffold also can present as a proper vitality support for the cells in hostile inflammatory wound environment.

To demonstrate the proliferation and distribution of MSCs and aMSCs (alternative MSCs) on Integra scaffolds in vitro. The, a MSC loaded scaffold was applied to a preclinical diabetic non-human primate wound model. Early microvascular perfusion changes were followed with laser Doppler, MSC migration with confocal microscopy on serial biopsies and early wound VEGF level.

A method to repair a wound in a mammal includes:
(a) activating the mammalian mesenchymal stem cells with an inflammatory cytokine, preferably interferon gamma (IFN-γ); and
(b) administering the activated mammalian mesenchymal stem cells to the mammal at a location wherein a wound can be repaired. Activating was achieved by a high dose of interferon gamma/ml, wherein a high dose is greater than 50 units interferon gamma/ml. a preferred dose is about 2,000 or 5,000 units administered for 2 hours, or 500 units administered twice during a 6 day period.

The mesenchymal stem cells were from bone marrow, e.g., human bone marrow, but other sources are suitable such as placental or adipose tissue. Administering may be approximately at the time of, or after the wound.

A composition that improves the outcome of wound repair, includes mammalian, e.g., human mesenchymal stem cells, activated by an inflammatory cytokine, e.g., IFN-γ. The composition is also useful to initiate angiogenesis and may be administered to a subject in need of tissue regeneration or wound repair. The composition is useful for the preparation of a pharmaceutical composition for repairing wounds in a mammal.

A method to produce activated mesenchymal stem cells for use in tissue repair includes:
(a) obtaining mesenchymal stem cells; and
(b) activating the mesenchymal stem cells by culturing the cells with an inflammatory cytokine e.g. IFN-γ.

Activating is achieved with a dose greater than 50 units interferon gamma/ml given at least 2 successive pulses of exposure to >50 units/ml IFN-γ within a 3 day-7 day period.

BRIEF DESCRIPTION OF THE DRAWINGS

FIG. 9.(A) is a staining of CD31+ cells (PE is red stained), white arrows show clusters of CD31+ staining cells in heart endothelium) in allogenic graft and (B) autologous interferon gamma activated MSC treated recipient's graft 7 days after transplantation (40×). (IIFC-FR with anti CD 31 rat monoclonal antibody PE conjugated 1:50 dilution, Abcam);

FIG. 9(B) is a quantitative analysis of CD31+ signal in transplanted heart. Fluorescence signal positive objects were counted in 5 standard ROI in 3 sections of each graft (n+2) in the following MSC treatment, donor MSC treatment, no MSC treatment and naïve non transplanted graft. MSC exposed to 6 or 7 days of high dose IFN-gamma show significantly higher numbers of endothelial cells within the transplanted murine heart allograft when compared to no treatment or non-activated MSC. When compared to non-treated or non-activated MSC treated [FIG. 9(A), left panel], recipients of activated MSC show increased CD31 staining in allogeneic transplanted hearts when studied 7 days after transplant [shown in arrows, right panel, FIG. 9(A)]. The number of CD31+ cells were measured using confocal microscopy and compared to naïve hearts which were never transplanted, hearts treated with no MSC, and hearts treated with either activated donor or host derived MSC [FIG. (9)B]. There was a statistically increased number of CD31+ cells when compared to control groups. In addition, when comparing the number of endothelial cells in MSC treated grafts to naive hearts, there was and no significant difference between these two groups, suggesting that MSC-induced repair and regeneration was promoting an allograft condition which most resembled a naïve, non-transplanted heart.

FIGS. 10 (A) & (B) MSC exposed to 6 or 7 days of high dose IFN gamma induce tolerance to allogeneic heart transplants, whereas non-activated MSC do not. B6 MSC were administered to B6 recipients of Balb hearts. Donor MSC and non-activated MSC prolonged survival for up to 40 days, however no tolerance was observed [FIG. 10(A)]. When rapamycin was added for a 5 day course post-transplant, this treatment alone did not lead to tolerance. When rapamycin was combined with activated MSC, greater than 100 day survival was achieved leading to tolerance of the heart allografts [FIG. 10(B)].

DETAILED DESCRIPTION

Surprisingly, inflammatory cytokines serve as initiating stimuli for mesenchymal stem cell (MSC) immunosuppressive activity in vivo.

With ex vivo exposure to a well-defined, inflammatory signaling, MSC can be induced to promote the induction of alternatively activated M2 macrophages, host macrophage activity, and promote the induction of large quantities of tregs when compared to MSC not exposed to inflammatory signaling, thereby resulting in greater efficiency to promote regeneration in conditions of aging or other conditions in which tissue regeneration is impaired and to reduce tissue damaging inflammation. This powerful in vivo effect, is in part, due to the recruitment and enhanced activity of host macrophages, which in conditions of aging and other conditions in which tissue regeneration is sub-optimal, are not optimally functional.

EXAMPLES

Examples presented are illustrative of the invention, not limiting.

Example 1

Reversal of Age-Related Decrease in Wound Healing

Figure 12A:
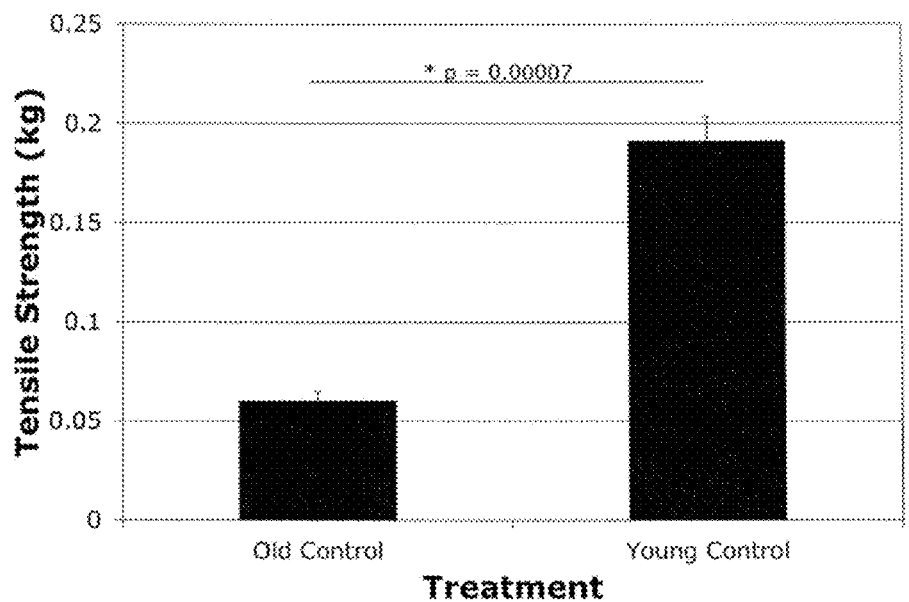
FIG. 12(A) shows that on day 8 tensile wound strength was determined in old and young mice; (B) a logarithmic dose schedule tested the effect of activated (aMSC) and naïve (nMSC) MSC on tensile strength in young animals at 7 days; (C) the optimal dose, $5 \times 10^4$ cells/wound was tested for significance of persistence of effect at 14 days.
Figure 12B:
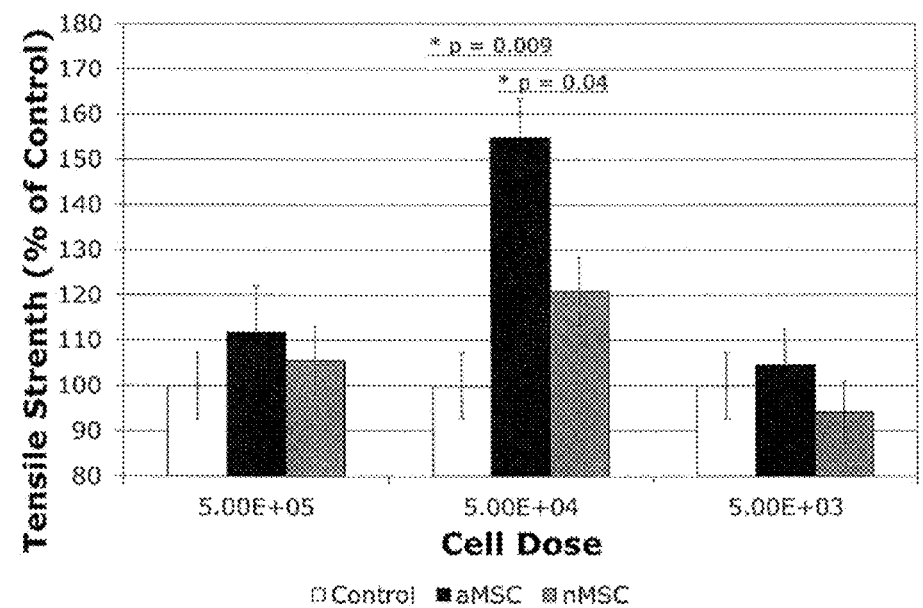
Figure 12C:
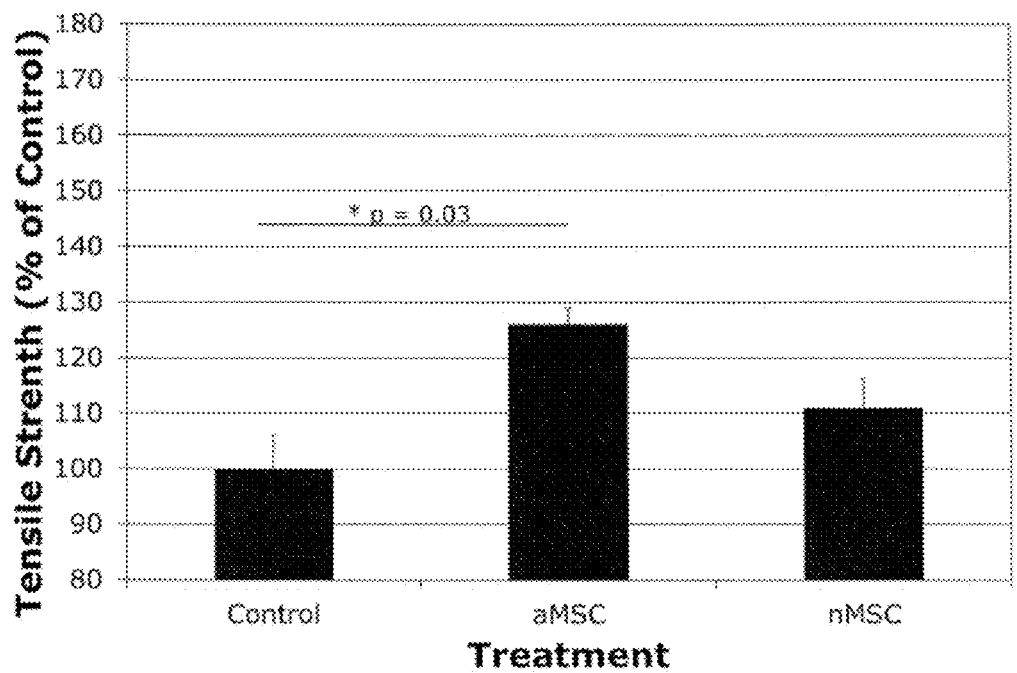

Wound tensile strength was tested in both young and aged mice to determine the effect of aging on tensile strength. In old mice, wound tensile strength was significantly diminished when compared to young mice, p=0.0007, FIG. 12(A); mean forces required to disrupt wound integrity in the young animals were roughly 4-fold higher than the aged mice. While animals were aging (approximately 16 months), a dose response curve deploying a logarithmic dosing schedule was performed in young mice to demonstrate the efficacy of naïve and activated MSC by successively increasing dose, FIG. 12(B). In this incisional wound system, in which wounds were treated with a single dose of MSC and excised on day 7, some efficacy was observed at the highest dose tested however the greatest efficacy was noted to be 5×104 activated MSC per 8 cm2 of wound area or 6,250 cells/cm2. Such an effect persisted to day 14, FIG. 12(C). This dose is substantively lower that those reported by others in experimental models and clinically for their effects on wound healing 4, 18-22. A variety of culture and isolation techniques exist in mesenchymal stem cell preparations demonstrating 24 It is speculated that this heterogeneity in culture in both form and function 23 heterogeneity results in non-uniform potency, leading to the necessity of increased cell doses to achieve efficacy. MSC therapy in a clinical wound healing application has tested efficacy of up to three applications of $2 \times 10^6$ cells per cm2 with higher doses leading to increased efficacy 21. These higher doses could have been necessary due to the topical nature of application and the observation that efficacy was tied to wound closure, not tensile strength. In an experimental animal model of incisional wounding and subsequent tensile strength measurement, 1.5×106 cells were deposited into the wounds with good effect 25. Based on such previous reports, the discrepancy in absolute numbers deposited into the wound is significant, suggesting activation prior to administration can substantively lower the number of cells required for biologic effect in young animals and humans.

Figure 13:
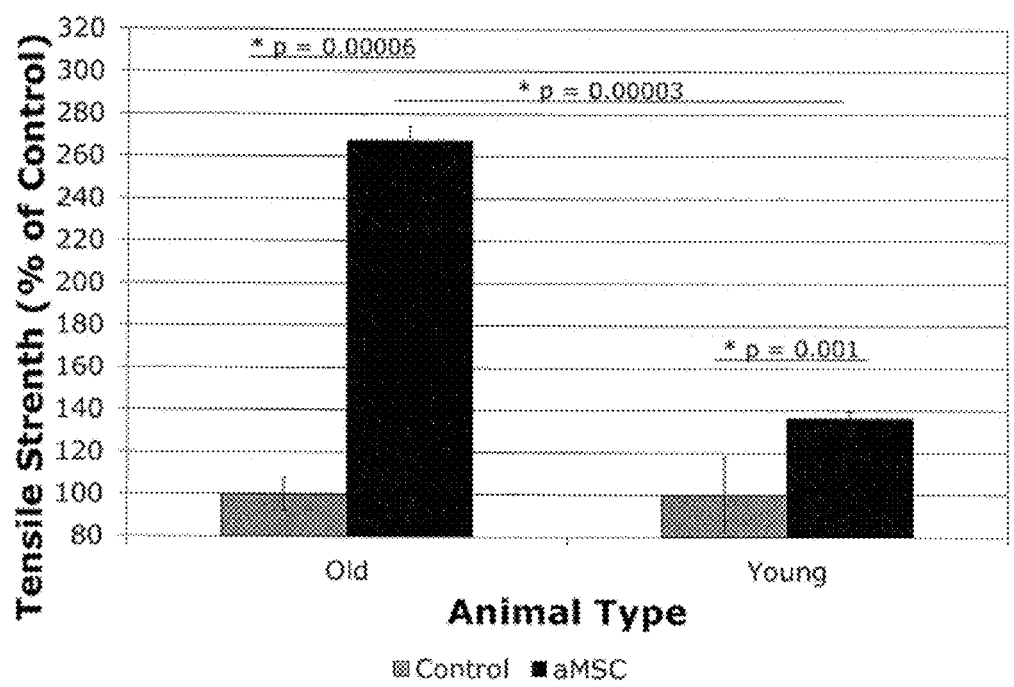
FIG. 13 shows the effect of activated MSC (aMSC) administered as a one-time dose into the 8 cm$^2$ wound base ($6.25 \times 10^3$ cells/cm$^2$) on tensile strength in both young and old animals.

Administration of the optimal dose, 5×104 MSC per wound, was tested in three separate experiments, (n=6) in which old and young animals were treated simultaneously for direct comparison, holding the variables of time, facility conditions, and MSC preparations constant (FIG. 13). Wounds were excised on day 7 for histologic examination. There was no evidence of CFDA labeled MSC at this timepoint; in contrast, at 2 days post-wounding, rare MSC could still be observed in the wounds (data not shown). Aged mice demonstrated a significant increase in tensile strength when compared to vehicle control; wounds of old animals treated with activated MSC had a mean tensile strength of 0.167+/−0.02 while vehicle treated aged animals had a mean tensile strength of 0.049+/−0.006, p=0.00006. In contrast, young animals achieved an increased tensile strength of 0.263+/−0.03 with activated MSC which was significantly higher than young animals treated with vehicle control, 0.170+1−0.02, p=0.001. Given that aged animals started at far lower baseline tensile strength with vehicle control, the response to MSC was relatively more pronounced in aged mice than in young mice, with aged mice increasing tensile wound strength 270+/−18 Wo and young mice increasing the tensile strength to 135 Wo of the vehicle control; a p value of 0.00003 demonstrated a significant difference in response to activated MSC between the aged mice and that of the young. Last, statistical comparison of MSC-augmented mean tensile strength of aged wounds to tensile strength observed in young animals treated with vehicle control was not statistically different. This finding indicates that activated MSC treatment restored the tensile strength of the aged mouse to that of a young mouse.

Figure 14A:
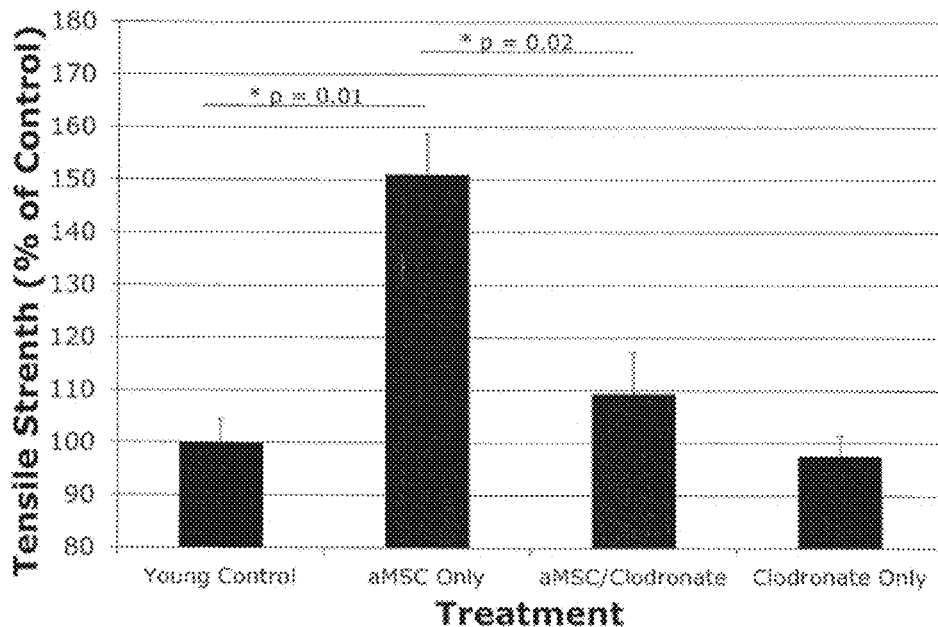
FIG. 14 shows liposomal clodronate depletion of host macrophages begun 7 days prior to MSC treatment was undertaken for effect on wound tensile strength in (A) young and (B) aged mice.
Figure 14B:
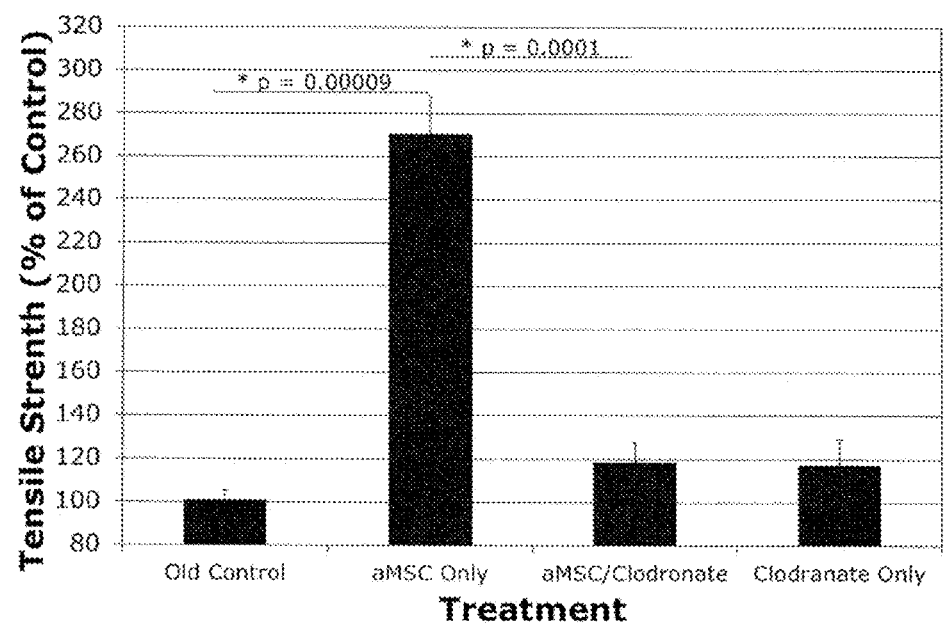

Based on the impaired macrophage function noted in the wounds of aged skin and the observation that MSC can divert pro-inflammatory macrophage function to an immunosuppressive function with greater phagocytic properties, host macrophages were depleted to define whether MSC might mediate their beneficial effect through these cells. In both young (FIG. 14(A)) and old (FIG. 14(B)) animals, treatment with liposomal clodronate abrogated the MSC effect, returning tensile strength to resemble that of vehicle control. These data suggest that in both young and old animals, MSC appear to mediate their effect on wound tensile strength through host macrophages. These observations may be explained by the ability of MSCs to promote conversion of pro-inflammatory, classical macrophages to alternatively activated macrophages. As opposed to the inflammatory role of classically activated macrophages, alternatively activated macrophages demonstrate more reparative abilities demonstrated by the increased production of IL-10 7 and the inhibition of pro-inflammatory interleukin IL-113 and IL-17 26. Alternative macrophages have also been shown to enhance extracellular matrix components such as collagen type I, collagen type III, matrix metalloproteinase (MMP)-1, tissue inhibitor of matrix metalloproteinase (TIMP)-1 and TGF-b1 27. Last, MSC-exposed macrophages have increased phagocytic capabilities which can be requisite for initiating reparative responses in the wound. Given the increased efficacy of activated MSC in aged mice when compared to young mice and the impaired function of macrophages observed in aged mice, activated MSCs likely reverse impaired macrophage function, thereby restoring the reparative process to that of young animals. In conclusion, activated MSC appear to reverse the effects of aging on wound tensile strength through their effects on host macrophages. These data support further development activated MSC therapies for enhanced tissue regeneration, especially for older population groups.

Example 2

Isolation of MSC by Rapid Immunodepletion

Murine MSC were isolated using rapid immunodepletion of macrophages. This technique also avoided long-term exposure of primitive MSC to mature myeloid lineages, which may enable murine MSC to become more immunostimulatory than immunosuppressive in vivo. These cells were observed to be capable of differentiating into adipogenic and osteogenic tissues.

Example 3

Figure 15:
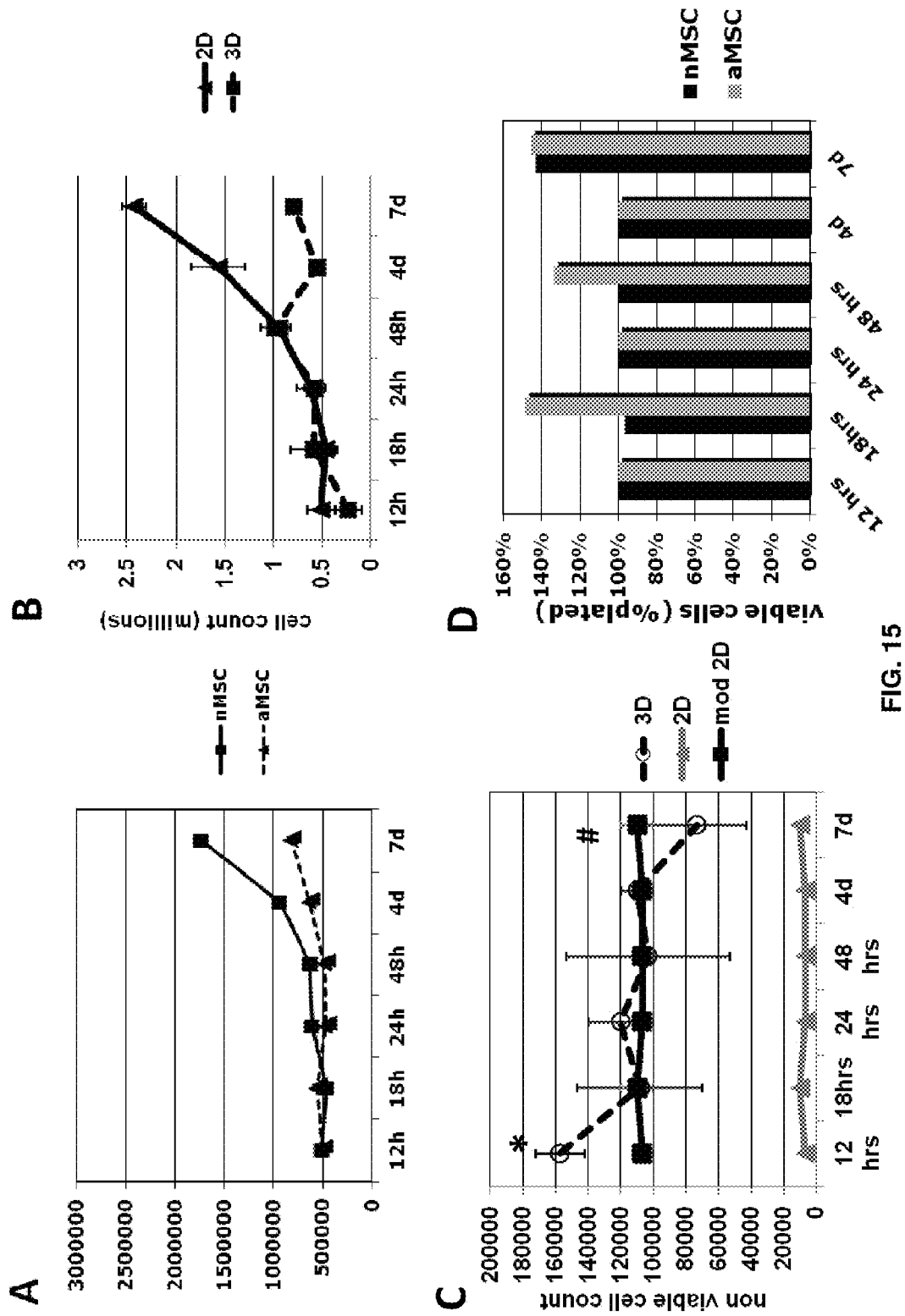
FIG. 15 (A) Proliferation of non-human primate naïve and activated MSCs on two dimensional culture conditions (185 cm$^2$ flasks); (B) Proliferation of non-human primate naïve MSCs on 2D culture conditions and on 3D Integra scaffold (*p<0.05 v. proliferation on scaffold); (C) Non viable cell count on 2D and Integra 3D cultures. Non viable MSCs on Integra were counted after scaffold digestion on different timepoints (dashed line). Non viable MSC on 2D culture were counted after cell harvesting from flasks (grey line). Due to the difference of two cell harvesting method, correction factor were applied on 2D cell counts (mod 2D, black solid line). Cell mortality on scaffold were significantly higher (*p=0.001) 12 hours after seeding and significantly decreased (p=0.05) after 7 days respect to 2D culture mortality; (D) Comparison between activated and naïve MSC proliferation and vitality on 3D Integra scaffold.

Comparison of Activated and Non-Activated MSC Viability and Proliferation on 2D Cultures and on Integra Scaffold Normal and activated MSCs were cultured in same conditions (initial cell number 0.5 million, same culture media (25 ml), 7 day follow up) on 185 $cm^2$ two dimensional surface and on three dimensional Integra scaffold (6 $cm^2$ surface×0.3 cm) and monitored their proliferation and viability. Interferon gamma treatment reduces proliferation rate of MSCs in two-dimensional cultures in flasks (p=, FIG. 15A). When MSCs were loaded to the three-dimensional Integra scaffold, their proliferation capacity diminished as well, maintaining a steady state population [$p<0.05$, FIG. 15(B)]. The application of aMSC on Integra scaffold did not reduce further their proliferative capacity, they maintained viability as the initial population size throughout a week of in vitro culture [FIG. 15(D)]. On Integra scaffold MSCs established as early as 3 h after seeding in homogeneously distributed manner, cells attached to collagen fibers and achieved fibroblast-like shapes. After 3 hours of seeding, cells were resistant to "washing out" tentatives maintained long-term viability that validate Integra as a clinically feasible stem cell carrier to wounds.

Example 4

Local Early In Vivo Modification of MSC Distribution on Integra

Figure 16:
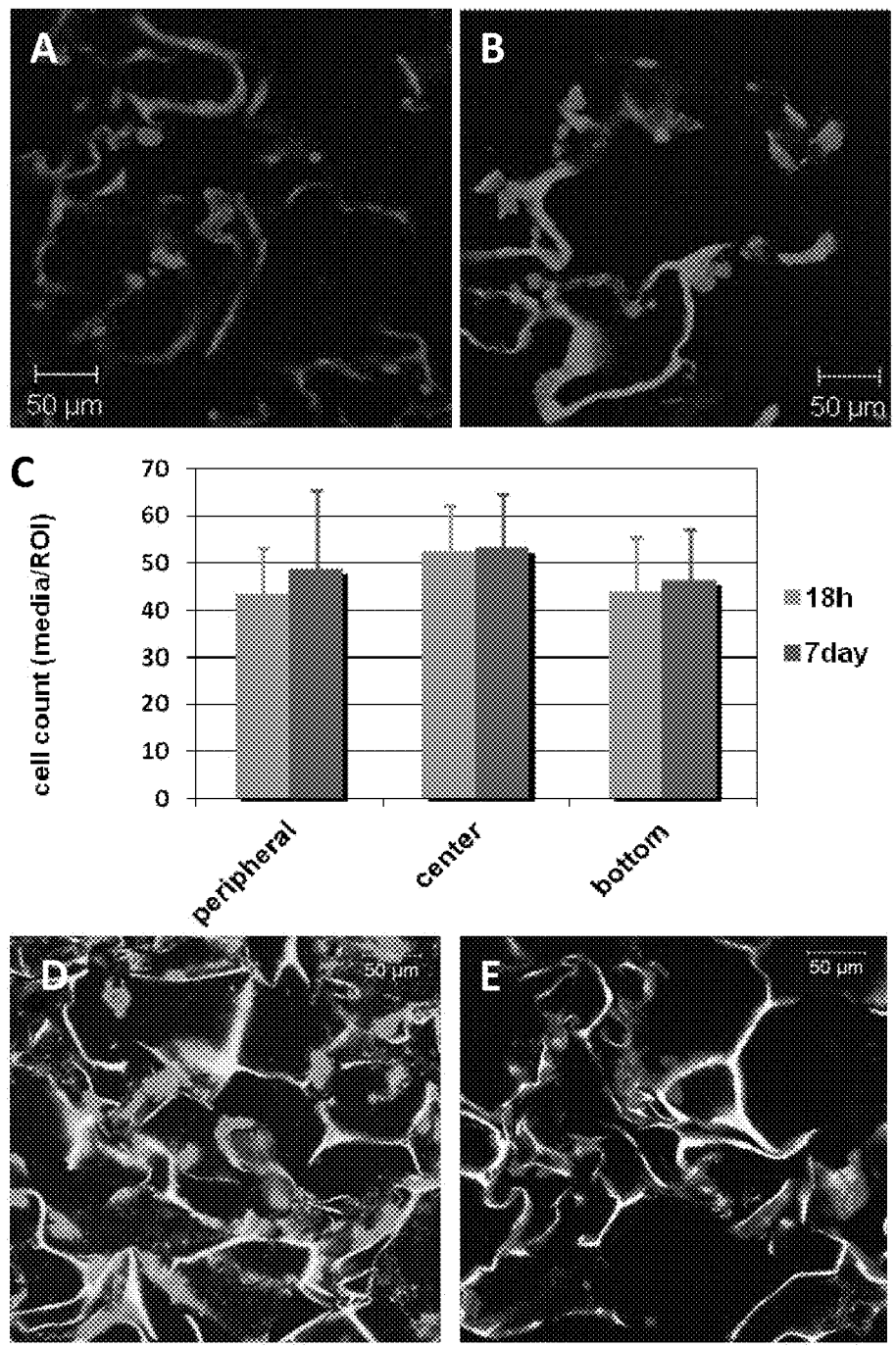
FIG. 16 Confocal microscope images of (A) medial and (B) peripheral zone of Integra scaffold loaded with naïve MSCs; (C) Cell counts of different regions of MSC loaded Integra at 18 h and 7 day timepoints; (D-E) Modification of cell distribution on peripheral and central regions of Integra 6 hours after in vivo application on NHP wound.

MSCs, when activated or not, in vitro distribute homogenously on Integra scaffold 12 hours after cell seeding [FIG. 16(A), (B)]. Cell counts and confocal imaging of Integra loaded with green fluorescent CFDA-SE labelled MSCs shows no significant differences between peripheral and medial regions in all three dimensions [FIG. 16(C)]. When the CFDA-SE-MSC loaded scaffold were placed to the diabetic wound in cynomolgus monkey (medial upper arm), cell distribution changed drastically in 6 hours (FIG. 2(D)-(E)): central regions showed nearly empty and peripheral parts touching the wound showed significantly higher number of fluorescent cells. The migration appeared from the upper peripheral region directing the peripheral region bellow in immediate proximity with the wound bed, as well.

Example 5

MSC Migration Outside from the Wound Bed

Figure 17:
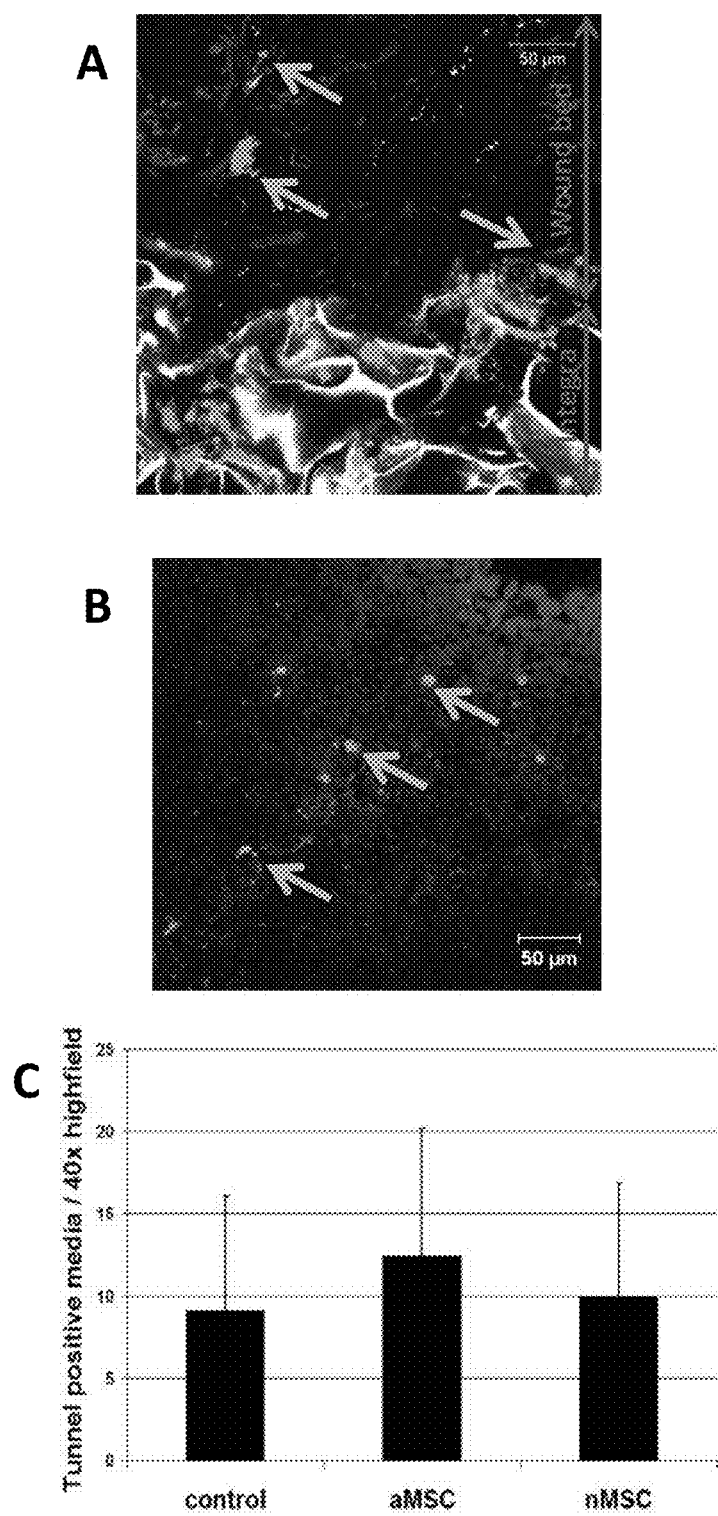
FIG. 17 Confocal microscope images of (A) wound bed and (B) axillary draining lymph node of wound covered with Integra scaffold loaded with aMSCs; (C) Tunnel positive cell quantification of draining LN (periferic region of 3 LN/each treatment group) of control, aMSC and nMSC loaded Integra covered wounds 6 h after in vivo placement.

MSCs migrated outside from the scaffold inside the wound bed [FIG. 17(A)]. Analysis of draining axillary lymph nodes of wounds with CFDA-SE-MSC loaded Integra showed the presence of MSCs (FIG. 17(B)). Comparison of TUNNEL positive and negative cell quantification (FIG. 17(C)) of draining lymph nodes of control, aMSC and nMSC treated wounds showed that no significant apoptotic cell accumulation appeared when drained MSCs were present. This finding suggests that viable MSCs actively migrate from the injured tissue to lymphoid tissue to exert their immunomodulative effect.

Example 6

In Vivo Early Flow Changes in the Wound Bed

Figure 18:
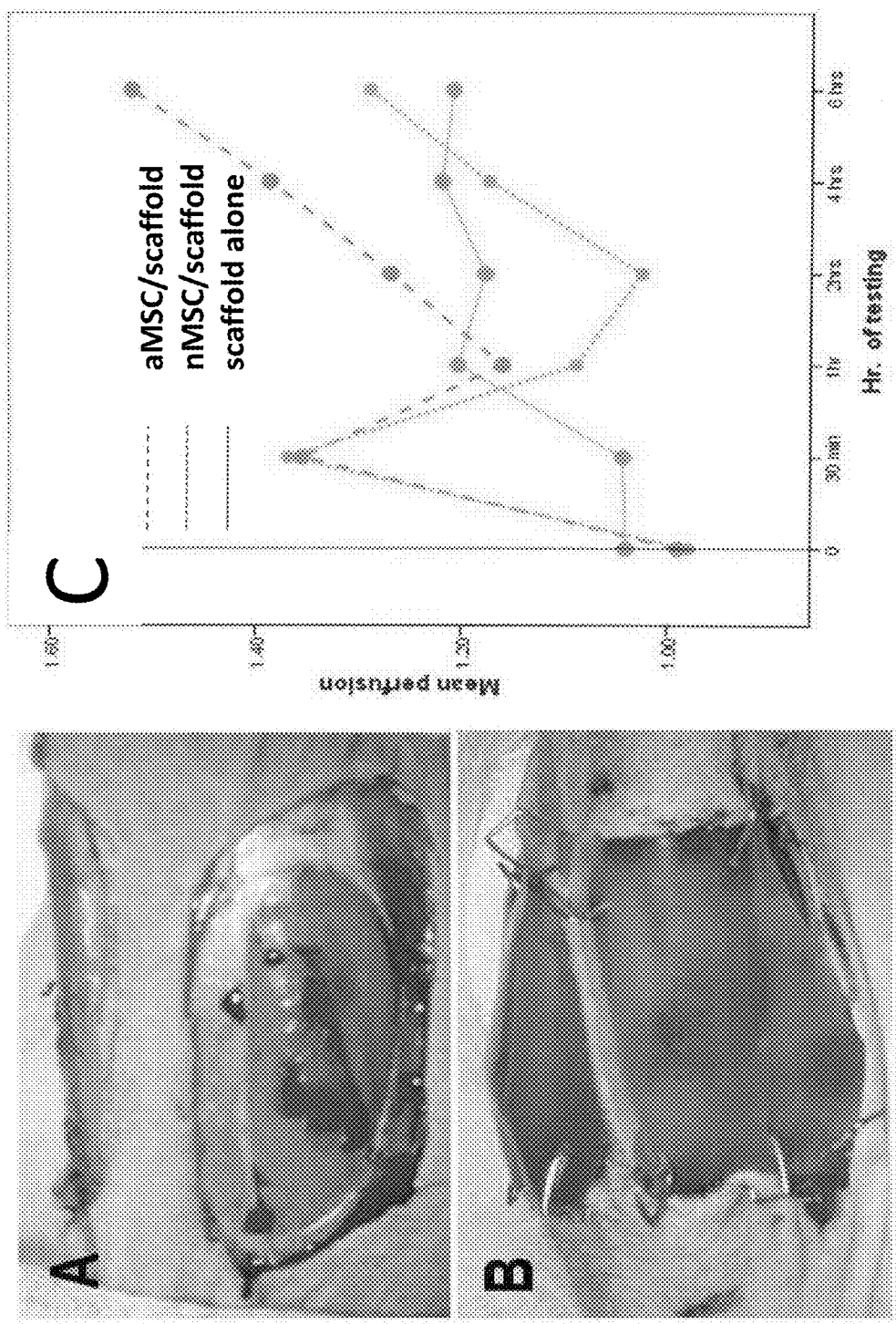
FIG. 18 In vivo Cynomolgous monkey wound on femoral medial and lateral region (A) before and (B) after Integra scaffold placement (C) Laser-Doppler follow up of wound bed microcircular perfusion flow changes.

Normal and activated MSC-loaded scaffold were applied to an in vivo non-human primate wound model [n=4, FIG. 18(A), (B)]. On diabetic Cynomolgus macacques (n=3) 2 cm×3 cm full thickness skin excision (until muscular fascia) wounds were performed on medial lateral side of femoral regions. Wounds were covered with a) sterile gauze with saline b) empty Integra c) nMSC loaded and d) aMSC loaded Integra. The mean perfusion flow of the wound, monitored by Laser-Doppler, increased rapidly and significantly in the first 30 minutes in wounds where cell-loaded Integra pieces were applied [FIG. 18(C)]. In the wounds with empty scaffolds, the perfusion increased slowly and gradually throughout the 6 hours of monitoring. After this first rapid peak of flow change, in wounds with normal and activated MSC loaded scaffolds the flow dropped in the next 30 min, still maintaining a higher flow values in aMSC-scaffold treated wound respect to control empty scaffolds. In the following hours all wounds had constantly increasing perfusion flow and aMSC treated scaffolds generated a significantly higher value of early blood flow at the end of the follow up (6 hours after surgery).

Example 7

Comparison of VEGF Levels of the Different Wound Beds

Figure 19:
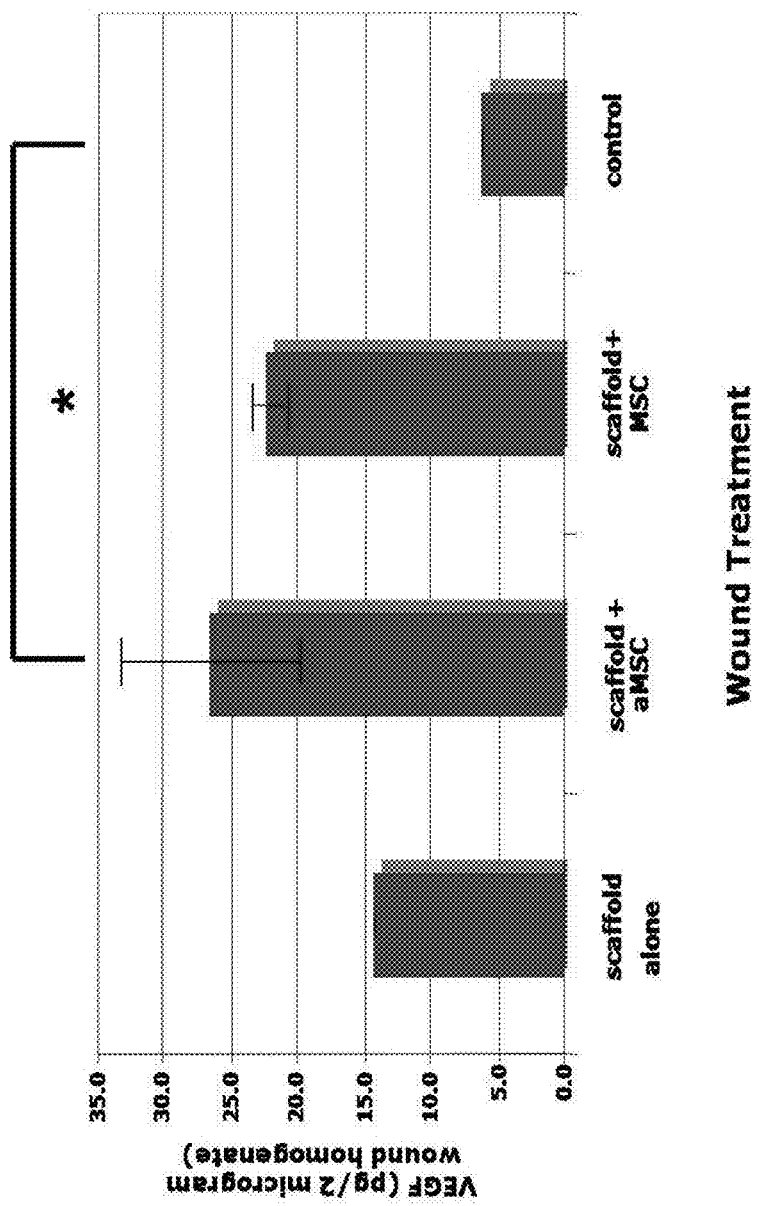
FIG. 19 VEGF content of wound bed tissue 6 hours after scaffold placement.

To test the proangiogenic effect of scaffolds and MSCs, six hours after the wounding, biopsies were performed on all experimental excisions to measure tissue levels of VEGF. Both wounds covered with activated and non activated MSC-scafold resulted in significantly higher level of VEGF (FIG. 19).

The wound bed VEGF content can be contributed to endothelial cells, residing or migrating macrophages or release from scaffolded MSC. As we previously described (mice wound paper), upon interferon-gamma activation MSCs produce increased amounts of VEGF. This suggests that our in vivo findings of proangiogenic microenvironmental change may be due to the direct paracrin effect of aMSCs and nMSCs in reaction to the interferon-gamma released in the host as acute inflammatory response.

Example 8

Graft v. Host Disease

Bone marrow isolated MSC activated by IFN-γ suppressed the development of graft versus host disease (GVHD) when given at the time of the bone marrow transplant as a preventive measure. Further, if given at later timepoints, it is 5 times more efficacious than non-activated MSC. IFN-γ activation was required to initiate MSC efficacy with a phenotypic change of MSC to express MHC Class II molecules remaining lineage negative. Cells remained devoid of expression of T, B, or macrophage cell surface markers, as well as the hematopoietic marker, CD45. IFN-γ induced MSC activation led to Class II expression on the surface of MSC.

MSC, pre-treated with IFN-γ, suppressed GVHD more efficiently than 5 fold greater numbers of MSC that were not activated. When given at the time of bone marrow transplantation, activated MSC prevented GVHD mortality (100% survival, p=0.006). MSC activation was dependent on the magnitude of IFN-γ exposure, with increased IFN-γ exposure leading to increased MSC suppression of GVHD. Activated MSC are a new strategy for preventing GVHD requiring smaller numbers of MSC.

Increased immunosuppressive properties of activated MHC Class II+ MSC can be useful in organ transplantation for the induction of tolerance or reduction of ischemia reperfusion injury, mitigation of autoimmune disorders.

Activated MSC provide increased deposition of matrix as well as pro-angiogenic factors. These qualities are likely to facilitate tissue regeneration as well as organ repair.

Figure 8:
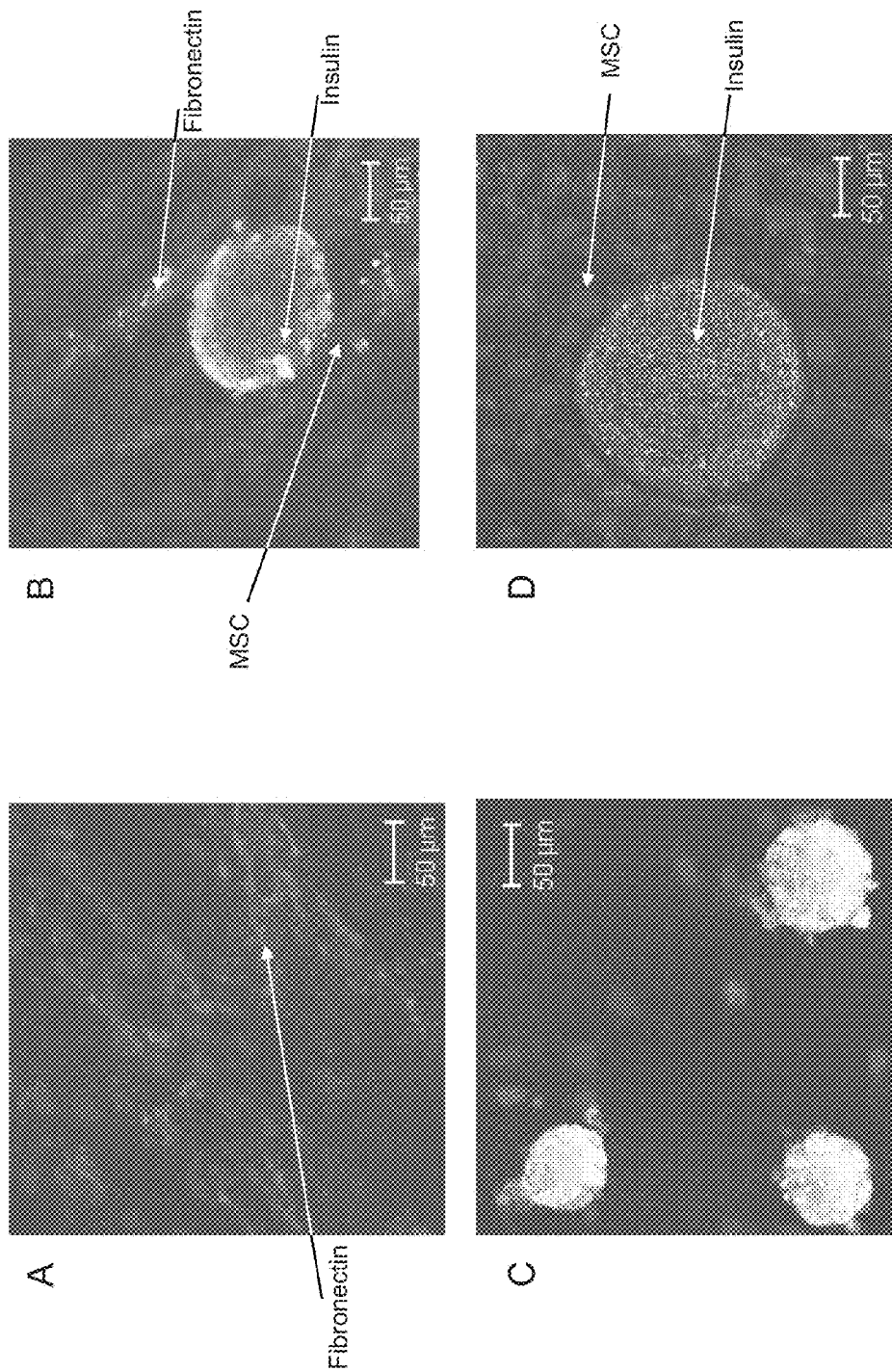
FIG. 8. (A) MSC stained for fibronectin (arrow) and DAPI (nuclei), (B & D) MSC-islet co-culture showing a single islet stained for insulin (arrow), fibronectin (arrow), DAPI (nuclei), (C) MSC-islet co-culture stained for insulin (arrow), and nuclear stain for MSC (arrow) after two day co-culture. MSC show a circular pattern of congregation around islets (C & D).
Figure 11:
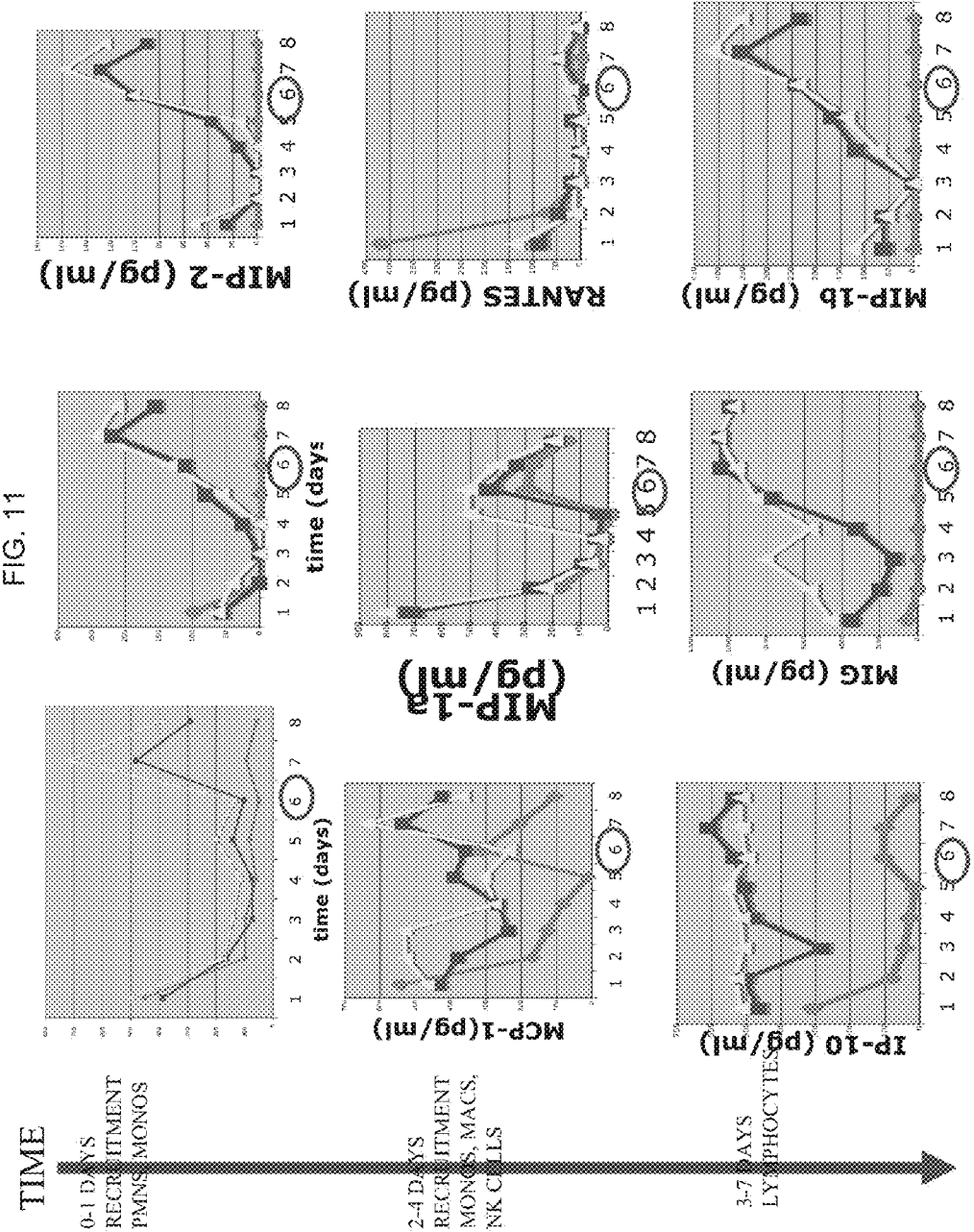
FIG. 11 show MSC exposed to 6 or 7 days of high dose IFN gamma show significant changes in functioning production of chemokines, cytokines and growth factors when compared to MSC exposed to lower (50 units/ml) or no IFN gamma. Specifically, in the first 24 hours following tissue injury as observed in wounds or following organ transplant, chemokines which recruit neutrophils and macrophages predominate. Interferon gamma activated MSC with either 50 units interferon (square), 500 units interferon (triangle) or no interferon gamma (diamond) demonstrate distinct differences in production of chemokines which recruit these cells, such as KC, LIX, and MIP-2, all of which are elevated at day 6 of incubation with interferon but show no baseline activity with non-activated MSC. In the next 3-7 days following tissue injury, lymphocytes are recruited to the site of injury with chemokines such as IP-10, MIG, MIP-1b. Once again there is a distinct difference in expression of these cytokines between MSC transformed with higher doses of intereferon gamma than those MSC with no interferon gamma These differences punctuate a functional difference in MSC exposed to high dose interferon gamma when compared to non-exposed MSC.

In studies with activated MSC, activation led to greater deposition of matrix. An example of how increased matrix might affect tissue regeneration is given in the studies undertaken with islets and MSC. Islet production of insulin is dependent on matrix. Therefore to test whether such increases in matrix by activated MSC could improve islet function, Murine Balb/c donor islets were isolated and co-cultured with C57/B6 MSC (FIG. 8). To test whether MSC co-culture resulted in increased matrix deposition, MSC-Islet co-culture (FIGS. 8B & D) was stained for fibronectin and compared by digital quantification to MSC (FIG. 8A) or islets alone. There was increased deposition of fibronectin when compared to non-activated MSC or islets alone, with fibronectin observed to congregate around the islet. MSC changed their wide distribution, migrating and binding to the islets (as evidenced by the lack of MSC in between the islets and the greater concentration of MSC around the islets) (FIGS. 8C & D). Islets co-cultured with MSC significantly increased insulin production when compared to islets alone in vitro. These data indicate that MSC can provide matrix structural support for transplanted tissues and the presence of this support aids in more efficient tissue function and regeneration.

Figure 7:
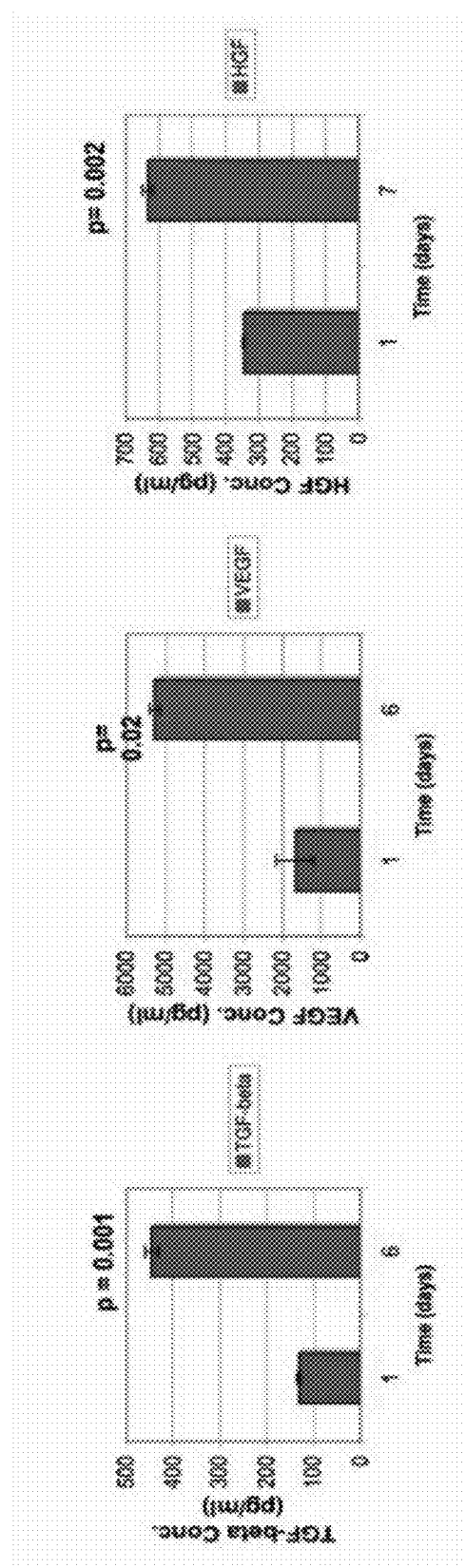
FIG. 7. MSC exposed to 6 or 7 days of high dose IFN-γ show significantly increased levels of the immunosuppressive cytokine, TGF-beta, and pro-angiogenic factors VEGF and HGF.

TGF-beta, VEGF, and HGF all significantly increase in production (FIG. 7) following activation with 6 or 7-day culture with IFN-γ. Using the 6 day co-culture with interferon gamma, these cells change in substance to express MHC Class II and to become more 1) immunosuppressive promoting GVHD prevention in vivo 2) produce greater amounts of chemokines attracting neutrophils, macrophages and then subsequently efficiently providing suppression of these cells within an allograft transplant, 3) induce high numbers of CD4 T-regulatory cells immediately after infusion, 4) express high amounts of pro-angiogenic factors such as VEGF, HGF.

A rapid immunodepletion method to isolate murine MSC resulted in dramatically and unexpected shortened culture times and low passage cells. Efficacy of the MSCs for GVHD treatment were similar to clinical observations, with lack of efficacy in prevention and improved survival when given during ongoing GVHD. To further dissect the factors which might initiate MSC suppression of GVHD, their earliest timepoint of efficacy was localized to occur following antigen presentation. Because IFN-γ is produced by donor T cells in response to antigen recognition, it could initiate MSC efficacy in vivo. A dose response effect was observed, with higher doses of IFN-γ being more effective than lower doses. IFN-γ serves as an initiating stimulus for MSC immunosuppressive activity in vivo. MSC response to this pro-inflammatory cytokine is differential, with three-log increases in IFN-γ required for maximal T cell suppression in vivo. MSC exposure to concentrated amounts of IFN-γ can stimulate MSC to prevent GVHD and provides the basis for a new strategy in prevention of GVHD.

Following analysis of recipient sera, sufficient serum levels were present to stimulate MSC on day 7. This suggests, that in the mouse model, this time period is likely to be effective for MSC activation. Correlation with IFN-γ serum levels in patients may guide the timing of MSC therapy. A lack of stimulating levels of IFN-γ was observed on days zero, one, or two. Threshold levels were present in areas where newly activated dendritic and T cells were producing high levels of IFN-γ locally, such as the spleen and lymph nodes. It has been reported that following administration, T cells migrate to secondary lymphoid organs and target organs which predominantly express certain chemokines and chemokine receptors, such as MIP-1 alpha, MIP-2, MCP-1, and MCP-3. MSC migration can also be enhanced by these chemokines and MSC chemokine receptor expression can be regulated by interferon gamma. Taken together, it is possible that, following infusion, MSC migrated in response to tissue chemokine expression, where local production of IFN-gamma by activated dendritic cells and donor T cells, during early GVHD (day 2) was sufficiently concentrated to provide MSC activation. Following activation, MSC have the capability to inhibit both dendritic cell and early T cell responses. It is possible that part of the efficacy of day 2 administration is due to the ability of MSC to dampen the escalation of GVHD by local control within both the target organs as well as the lymphoid organs. Of all the tissues examined, splenic tissue appeared to have some of the most significant improvement following MSC treatment. The powerful and seemingly preferential effect of MSC observed on this lymphoid tissue, may reflect the greater levels of locally produced IFN-$\gamma$ during GVHD.

MSC administered on day 30 had no efficacy when compared to day two or day 20. This observation may be due to two factors: the overwhelming increase in the number of donor T cells for which the number of MSC were insufficient and/or the corresponding drop in the levels of IFN-$\gamma$. Despite such increased numbers of T cells, T cell production of IFN-$\gamma$ has been observed to decrease during ongoing GVHD. In addition, low serum levels of IFN-$\gamma$ were observed. It is possible that MSC administered on day 30 failed to receive sufficient IFN-$\gamma$, either through the circulation or through local production. The lack of available IFN-$\gamma$ to MSC may have limited their ability to produce significant amounts of immunosuppressive molecules such as IDO, IL-10, TGF-$\beta$. All of these have been observed to have a dose response relationship with IFN-$\gamma$ treatment of MSC. In vivo observations are very similar to those observed in vitro; using this model, MSC-induced suppression of GVHD is dependent on the magnitude of IFN-$\gamma$ stimulus.

Addition of five-fold greater MSC, $0.5 \times 10^6$ MSC, improved survival to 85% when MSC were administered on day 20. When MSC were administered on day 2, survival remained at 60% despite the higher dose. MSC given on day 2 failed to receive sufficient amounts of IFN-$\gamma$ to become activated. Following activation of MSC, $0.1 \times 10^6$ MSC administered on day 2 improved survival to 100%. This observation suggests that the efficacy of MSC can be manipulated by IFN-$\gamma$ activation. Since IFN-$\gamma$ production can vary during the course of GVHD, the efficacy of MSC may also vary unreliably, with some treatments not attaining full immunosuppressive potential. Depending on the number of activated T cells, the ratio of T cells to MSC, and the available IFN-$\gamma$, it is possible that lack of optimization of these three factors could result in MSC therapy which is only marginally beneficial.

With the incidence of GVHD exceeding 50%, and success in GVHD prevention being limited, new strategies in preventing GVHD and its significant morbidity and mortality are needed. Prevention of GVHD with activated MSC may play a role in broadening the therapeutic potential of allogeneic stem cell transplantation.

One of the strategies for control and/or prevention of GVHD has been to induce a shift from TH1 to TH2 cytokines. Because IFN-$\gamma$ is a known stimulant of TH1 cytokine production, a potential harmful side effect from IFN-$\gamma$ MSC treatment might be the release TH1 cytokines, IL-2, GM-CSF, and TNF-$\alpha$. Analysis of day 1 and day 6 supernatants from MSC exposed or not exposed to 500 units/ml of IFN-$\gamma$ (Biosource, 20-plex cytokine detection kit, Invitrogen) showed undetectable amounts of TNF-$\alpha$ and GM-CSF and only modest increases in IL-2 from 50 pg/ml to 80 pg/ml in IFN-$\gamma$ MSC. Untreated MSC had undetectable amounts of all three TH1 cytokines. IFN-$\gamma$ had no effect on inducing IL-10 production, but significantly increased TGF-beta (p=0.001). TGF-beta has been implicated in T cell suppression by MSC. In response to IFN-$\gamma$, MSC may increase suppression and limit TH1 responses.

Example 9

Treatment of GVHD

Figure 1:
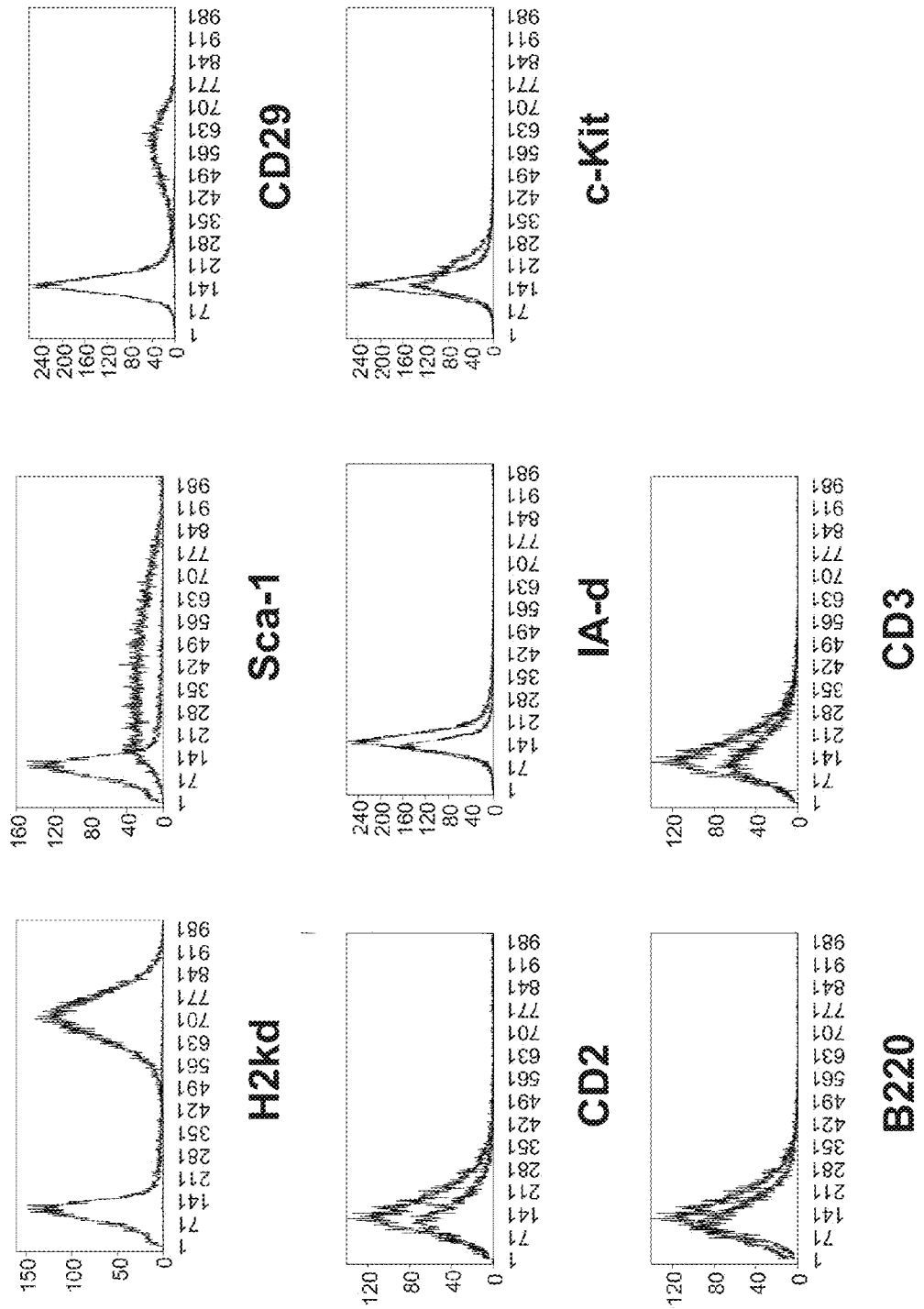
FIG. 1. MSC phenotype following rapid immunodepletion: when compared to isotype controls, MSC stained positive for mhc class i (h-2k$^d$), the vla complex marker cd29, the cell adhesion receptor cd44, and the hematopoietic stem cell marker sca-1. Mscs stained negative for mhc class ii (i-a$^d$), macrophage cell surface markers (cd11b, cd14), b cell marker (b220), lymphocytes (cd2, cd3, cd4, and cd8a), and the hematopoietic stem cell markers thy-1 and c-kit. histograms represent consistent findings after greater than 30 isolation experiments.
Figure 1:
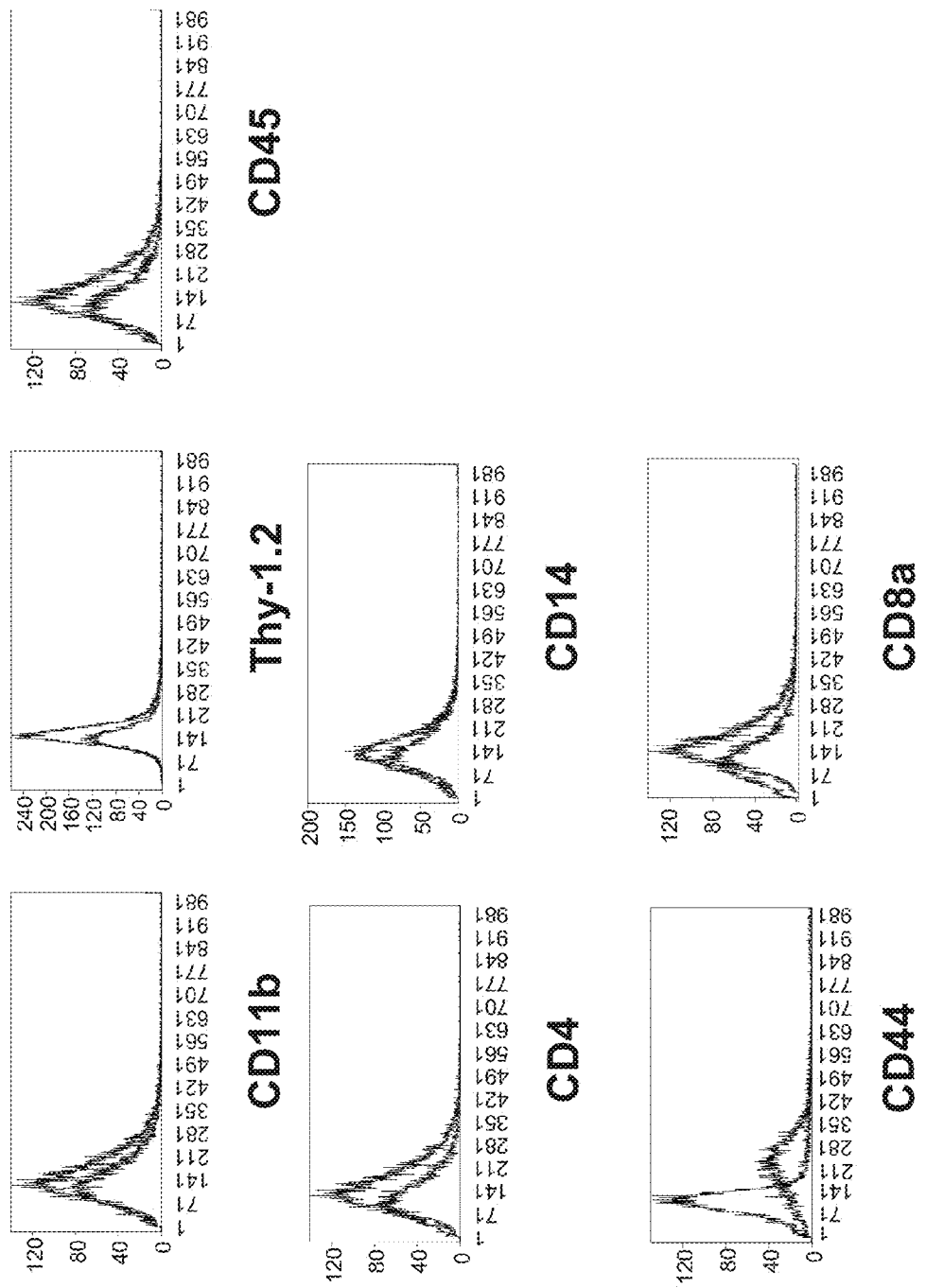
Figure 2:
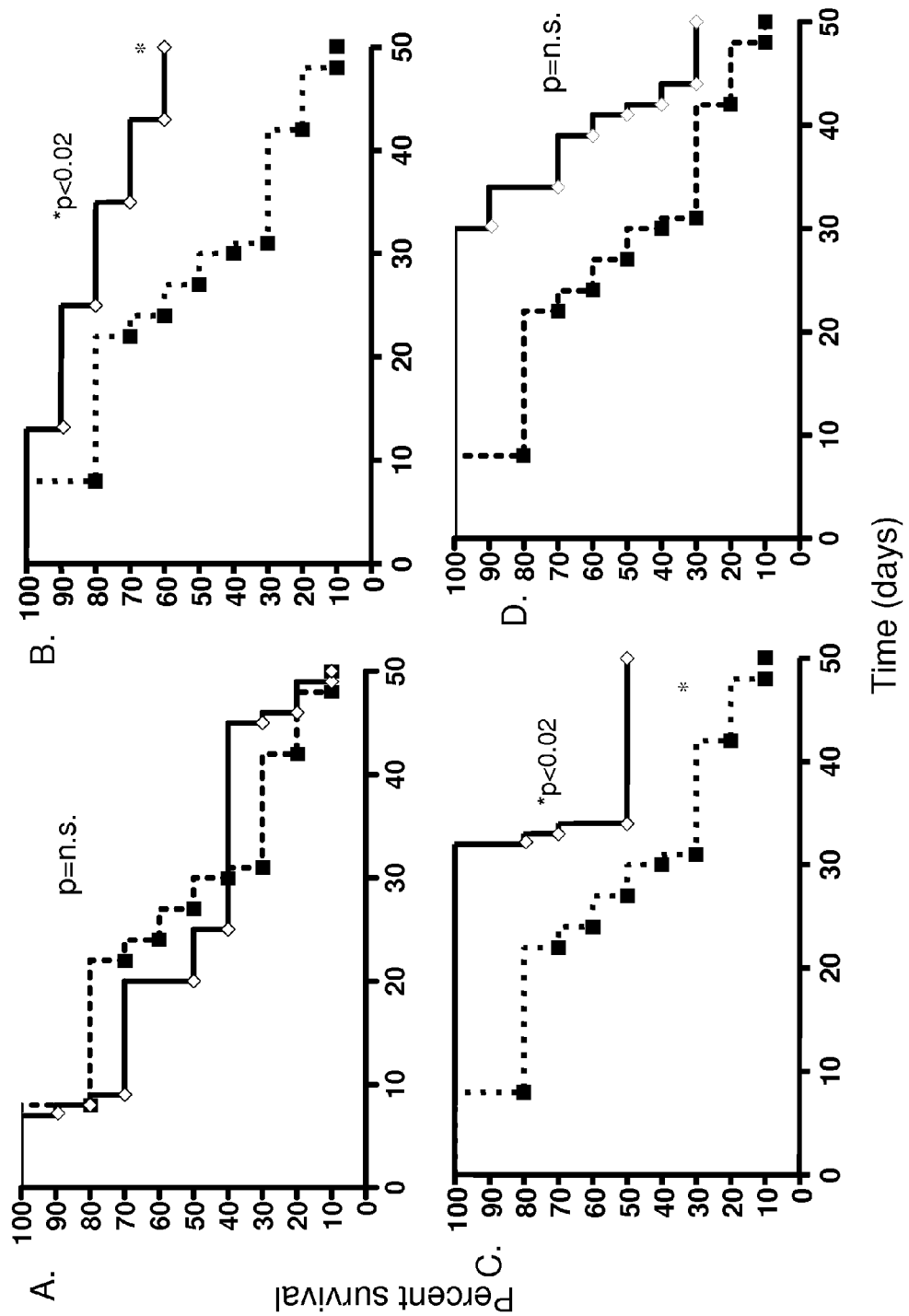
FIG. 2. The effect of timing of MSC administration on 40-day survival following induction of GVHD. Following lethal irradiation, B6 recipients underwent transplantation with allogeneic Balb BMC and splenocytes on day 0 (control, solid line) resulting in 30% survival, (experiment repeated 6 times, n=20). In experimental groups (dashed line), Balb MSC were administered on days 0 (2A), 2 (2B, n=20), 20 (2C) or 30 (2D). MSC administered on days 2 and 20 significantly increased survival from 10% to 60% and 10% to 50%, respectively ($p<0.05$).

To establish whether MSC isolated according to the methods disclosed herein proved efficacious in the treatment of GVHD, $0.10 \times 10^6$ MSC were administered during various phases of GVHD. First, MSC were administered on day 0 along with the bone marrow graft and supplementary T cells to induce GVHD (FIG. 2A). For this administration, MSC were co-cultured with the bone marrow graft and splenocytes for two hours prior to administration. Cell contact between MSC and GVHD-producing T cells prior to donor antigen recognition suppressed T cell activity and subsequent GVHD mortality. Pre-emptive cell contact of MSC with T cells did not prove to be effective; there was no statistical improvement in GVHD-related mortality when compared to control animals that received bone marrow grafts and supplementary T cells.

Example 10

Treatment of GVHD

During Phase II of GVHD, donor T cells are exposed to host antigens and become active, serving to both proliferate and recruit additional T cells. MSC, administered after donor antigen recognition, could mitigate GVHD mortality (FIG. 2(B)). Antigen recognition and/or subsequent activation of T cells appeared to be required for MSC efficacy since MSC given on day 2 increased survival from 10% to 60%, (p<0.02). Following MSC infusion, some of the animals that had developed signs of GVHD, such as ruffled fur and alopecia, had improvement of these physical findings. Many surviving animals experienced a complete reversal to normal appearing fur.

Example 11

Treatment of Ongoing GVHD

MSC were tested for their ability to treat ongoing GVHD (administered on day 20) or treatment of severe, pre-morbid GVHD (given on day 30). MSC administration increased survival from 10% to 50% when given on day 20 (p<0.02, FIG. 2(C)), and to 20% for day 30 treated animals (p=0.08, n.s, FIG. 2D). These data show MSC isolated with rapid immunodepletion are effective in preventing GVHD as well as treating ongoing GVHD. MSC contaminated with >3% CD45+ cells and MSCs of late passage (greater than 6), had no significant effect on GVHD-related mortality, indicating that early passage and significant immunodepletion were required for MSC suppression of GVHD.

Example 12

MSC Treatment is Dose-Dependent

Figure 3:
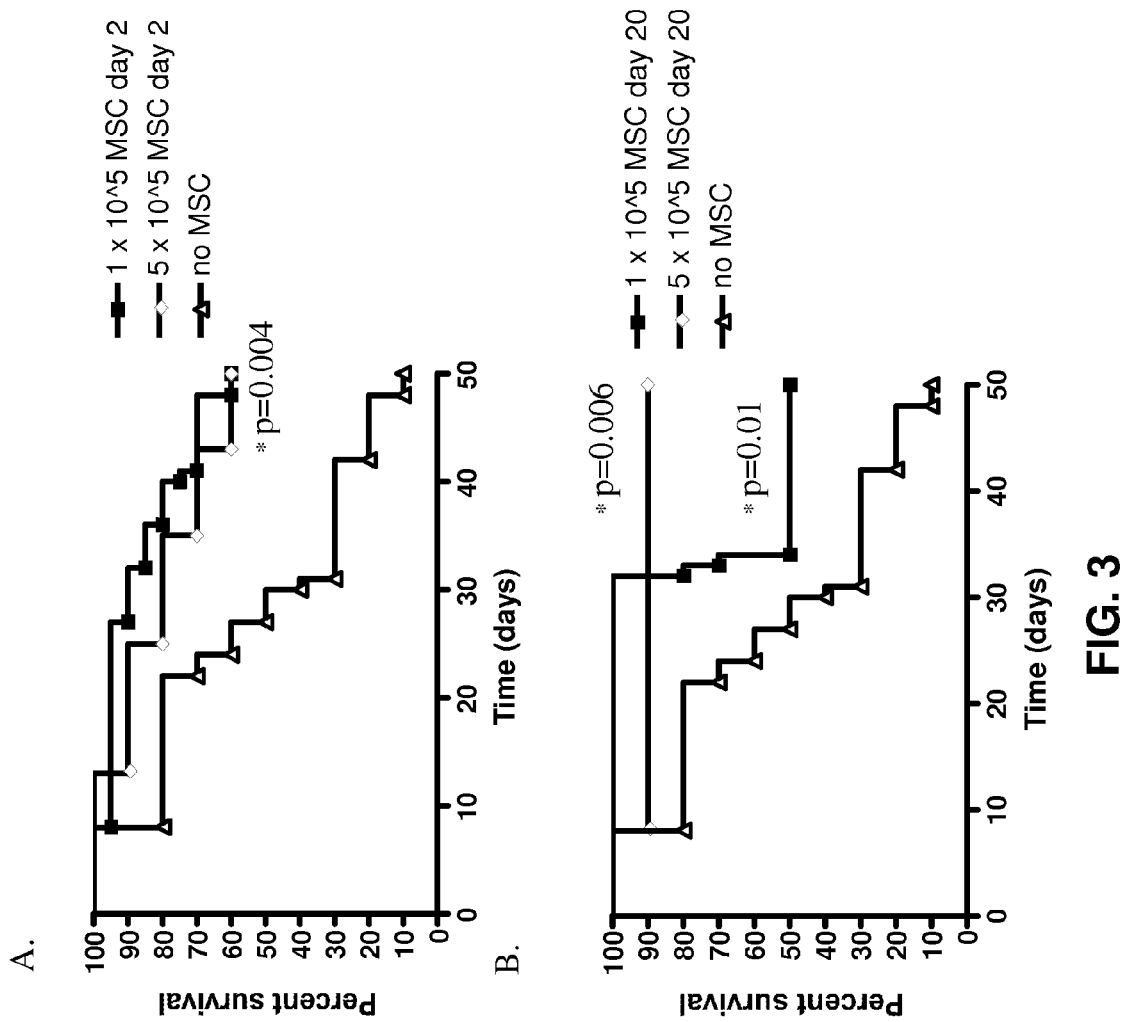
FIG. 3. Effect of MSC dose escalation. Low ($0.1 \times 10^6$) and high ($0.5 \times 10^6$) dose MSC were administered on day 2 (3A) or day 20 (3B). Both low and high doses led to a significant improved survival when given on either days 2 or 20. High dose MSC given on day 20 significantly increased survival to 85% ($p=0.006$), when compared to control animals.

To further define the limits of MSC efficacy, the effect of MSC dose on survival was examined. Following transplantation, either $0.1 \times 10^6$ or a five-fold greater dose, $0.5 \times 10^6$ MSC were administered on either day 2 or day 20 (FIG. 3) and compared to transplanted animals which did not receive MSC. There was no dose-response effect when a higher dose was administered on day 2. While both $0.1 \times 10^6$ and $0.5 \times 10^6$ MSC significantly increased survival (p=0.004), the two survival curves were indistinguishable from each other (FIG. 3(A)). These data indicated that higher doses, when given as a preventative measure, did not appear to change the course of mortality. For animals receiving MSC on day 20, survival following $0.5 \times 10^6$ MSC significantly increased from 10% to 85%, (p=0.0006, FIG. 3(B)).

Statistical comparison between low and high dose revealed a strong trend suggesting a difference between the two groups, (p=0.07). Based on these data, it appeared that MSC behaved differently when given for treatment than when given as a preventative measure. Because higher numbers of T cells are likely to have undergone antigen recognition and proliferation on day 20 when compared to day 2, the difference in MSC behavior was likely due to an increase in the magnitude of activating signals generated from the increased antigen presentation and/or T cell proliferative activity.

Example 13

Histological Findings

Figure 4:
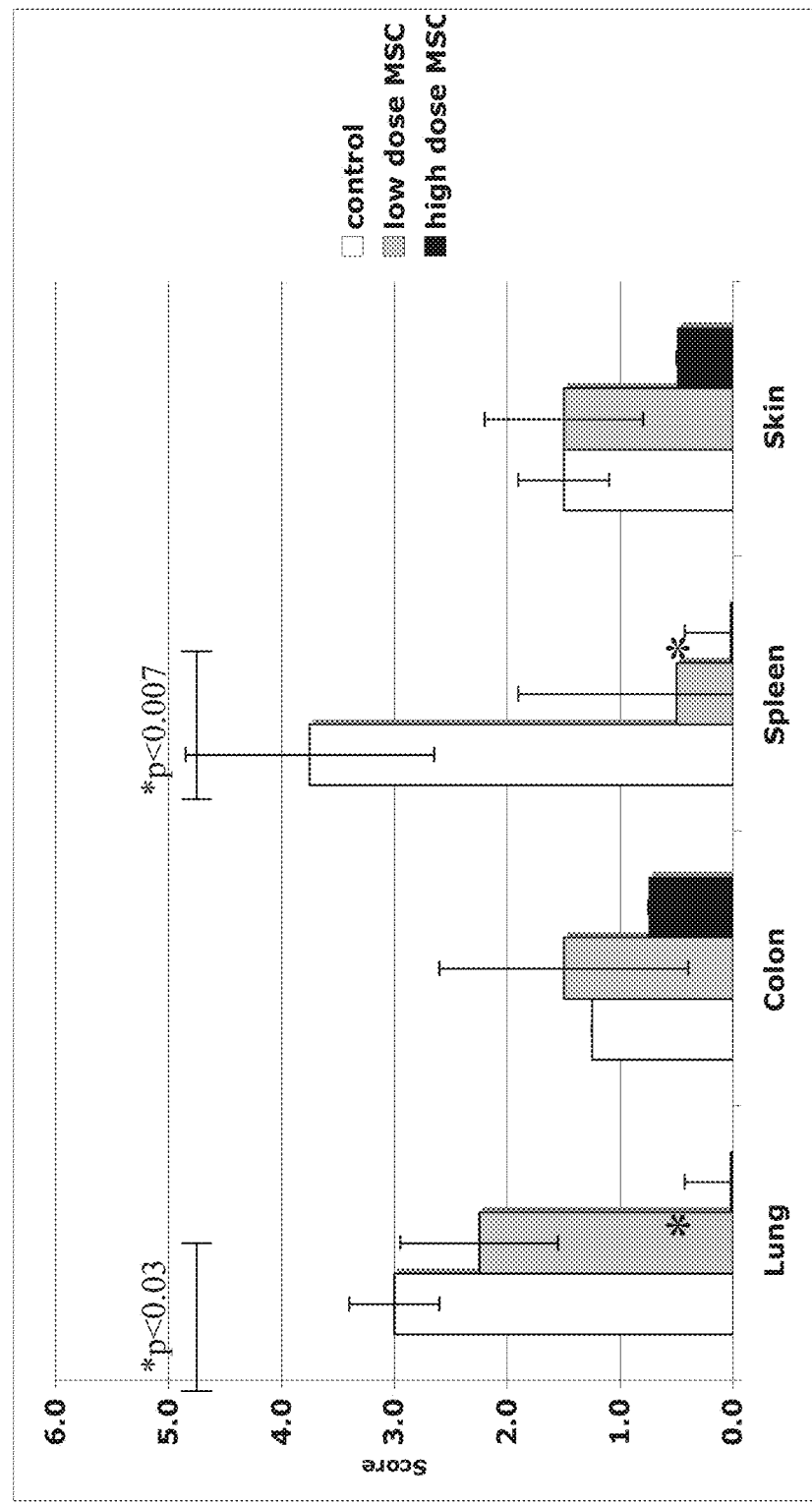
FIG. 4. GVHD scores of lung, colon, spleen, and skin. Recipients of $0.5 \times 10^6$ or $0.1 \times 10^6$ MSC and control recipients were euthanatized for histological examination. Sections taken from lung, colon, and spleen were scored on a scale of 1 to 4 with 4 being the most severe changes consisting with tissue destruction observed in GVHD. Skin was scored on a scale of 1 to 3, with 3 being the most severe. This experiment was repeated three times (n=3 per group).

Tissues were analyzed from recipients who underwent treatment with MSC. On histological examination of lung, spleen, colon, and skin, MSC treatment improved the severity of GVHD scoring. Spleen and lung displayed the greatest findings, with both tissues observed to be normal appearing after receiving $0.5 \times 10^6$ MSC (p<0.0007, and 0.03, respectively, FIG. 4).

Example 14

IFN-γ is Required for MSC Reduction of GVHD Mortality

To test whether antigen recognition and potentially, T cell proliferation was required to initiate MSC activity, the regulatory protein Interferon gamma (IFN-γ) was tested for its ability to initiate suppressive activity in MSC. This protein was chosen due to several considerations. First, IFN-γ can be produced by both donor dendritic cells following antigen recognition and donor T cells upon activation. In response to high concentrations of IFN-γ, MSC are induced to produce indoleamine 2,3-dioxygenase (IDO), the enzyme known to promote the immunosuppressive barrier at the maternal-fetal interface. Also, MSC treatment with IFN-γ in vitro has been observed to enhance MSC production of several immunosuppressive cytokines such as transforming growth factor-beta. MSC responded to the presence of this immunoregulatory protein by being stimulated to suppress GVHD.

Figure 5:
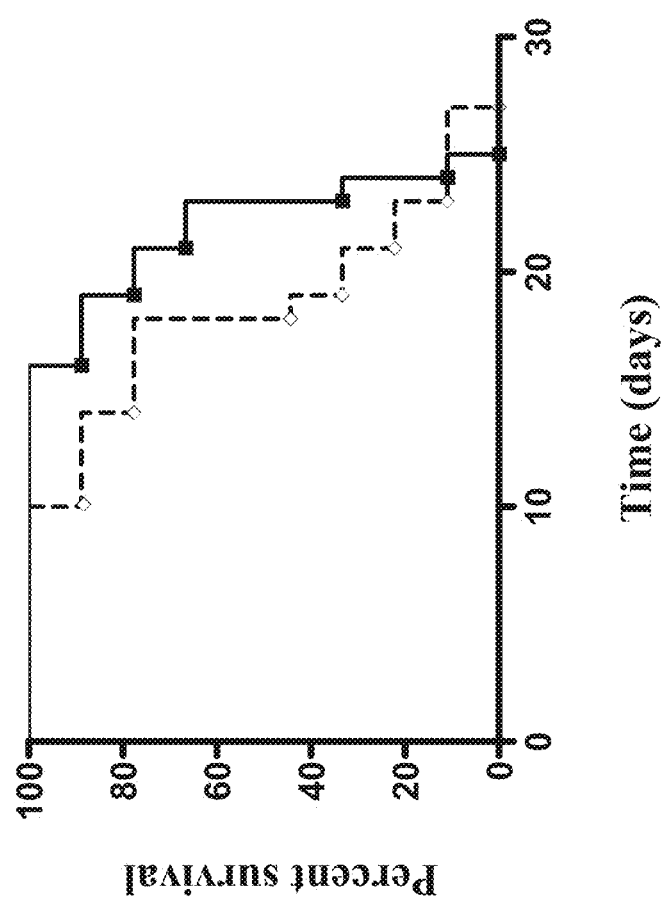
FIG. 5. Requirement of IFN-γ for MSC mitigation of GVHD. Splenocytes from IFN-γ knock out mice were used to induce GVHD (solid line). Addition of MSC on Day 2 failed to affect survival (dashed line), indicating MSC required IFN-γ to initiate their suppressive effects.

To determine whether IFN-γ played a role in MSC suppression of GVHD in vivo, donor splenocytes, incapable of producing IFN-γ, were infused to induce GVHD. In this system, the sources of IFN-γ were limited to the low numbers of antigen presenting cells within the bone marrow and host hematopoietic cells. GVHD-related mortality was rapid and severe; 100% mortality occurred prior to day 30 (FIG. 5). Addition of MSC had no effect. These data indicate that the absence of donor IFN-γ led to accelerated GVHD which could not be controlled by donor MSC.

Example 15

MSC Activation with IFN-γ

Figure 6:
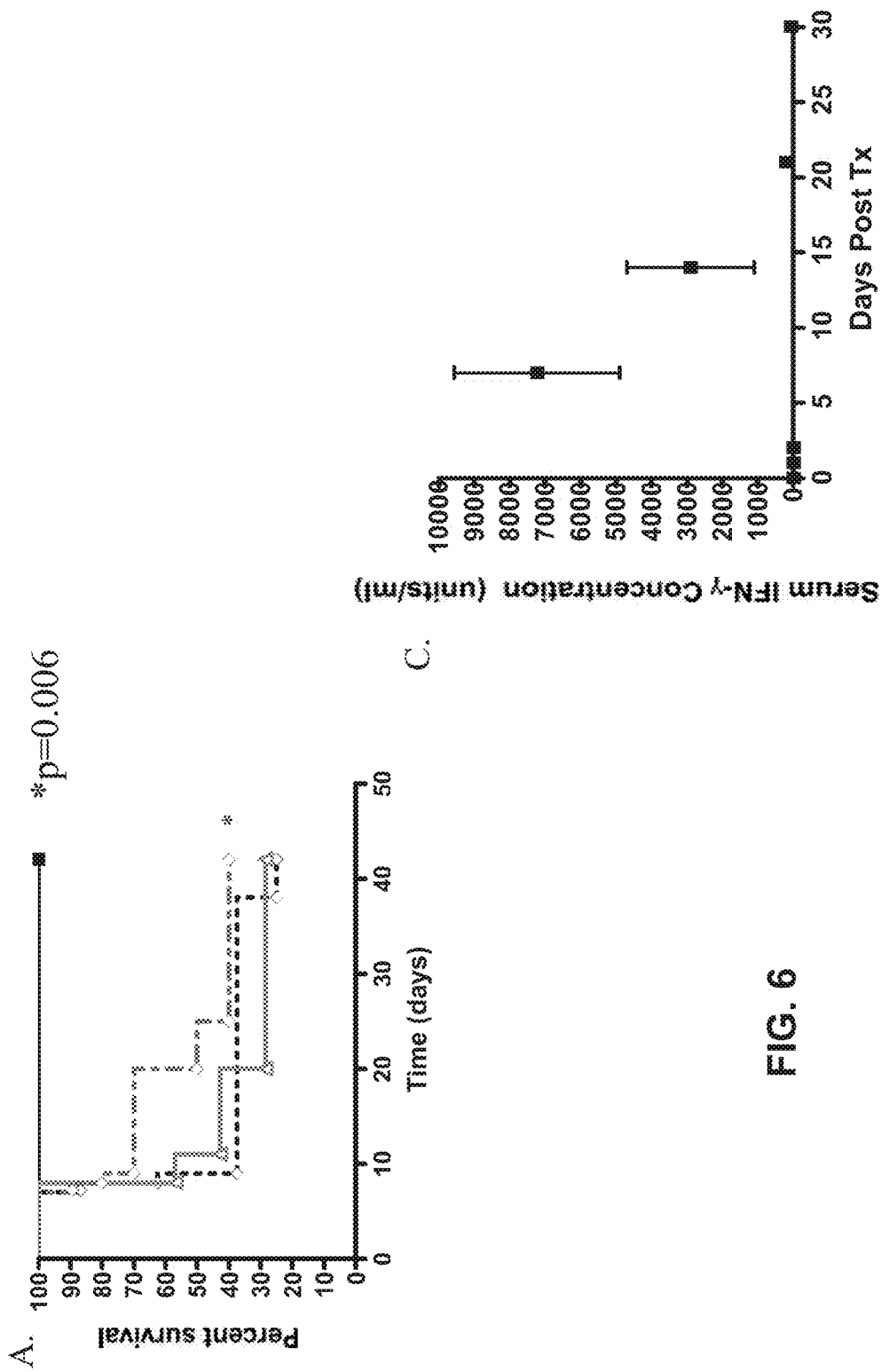
FIG. 6. Activation of MSC with IFN-γ. Either untreated (6A, dashed grey line) or IFN-γ treated Balb MSC were administered on day 0. MSC treated with 5 (solid grey line) or 50 units (dashed black) IFN-γ showed no effect on GVHD-related mortality when compared to untreated MSC. MSC treated with 500 units (solid black line) were significantly more effective than untreated MSC ($p=0.006$) and MSC treated with lower doses of IFN-γ. IFN-γ treatment appeared to have a direct effect on MSC, (6B), causing new expression of MHC Class II, changing both the phenotype and function of these cells. No detection of CD45 or CD11b populations were noted after IFN-γ treatment (grey line) when compared to pre-treatment (black line), indicating that IFN-γ treatment did not expand an immunoregulatory dendritic cell population, (experiment performed >10 times prior to each transplant). Following transplantation and the development of GVHD, circulating IFN-γ measured in the serum by ELISA (6C) surpassed 500 units by day 7 with a gradual drop below 500 by days 21 and 30 suggesting there was sufficient circulating IFN-γ to activate MSC by day 7, but not after day 30, (each timepoint represents analysis of 3-5 recipients measured in duplicate).

To further examine the ability of IFN-γ to initiate MSC suppression, MSC were treated with three concentrations of IFN-γ, 5, 50, or 500 units, prior to their administration on day 0. MSC might not be effective on day 0 because they failed to receive a sufficient IFN-γ stimulus. By pre-treating the MSC with IFN-γ, MSCs were activated for more efficient suppression of GVHD. When treated with either of the lower doses of IFN-γ, MSC were ineffective in significantly preventing GVHD mortality when compared to untreated MSC (FIG. 6(A)). In contrast, 500 units IFN-γ increased survival to 100%, (p=0.02) and this treatment was significantly better than MSC pre-treatment with 5 units (p=0.006) or 50 units (p=0.005). These data suggested that MSC suppression could be initiated with high dose but not low dose IFN-γ, thereby identifying a threshold of MSC activation in response to the immunoregulatory protein.

Figure 6B:
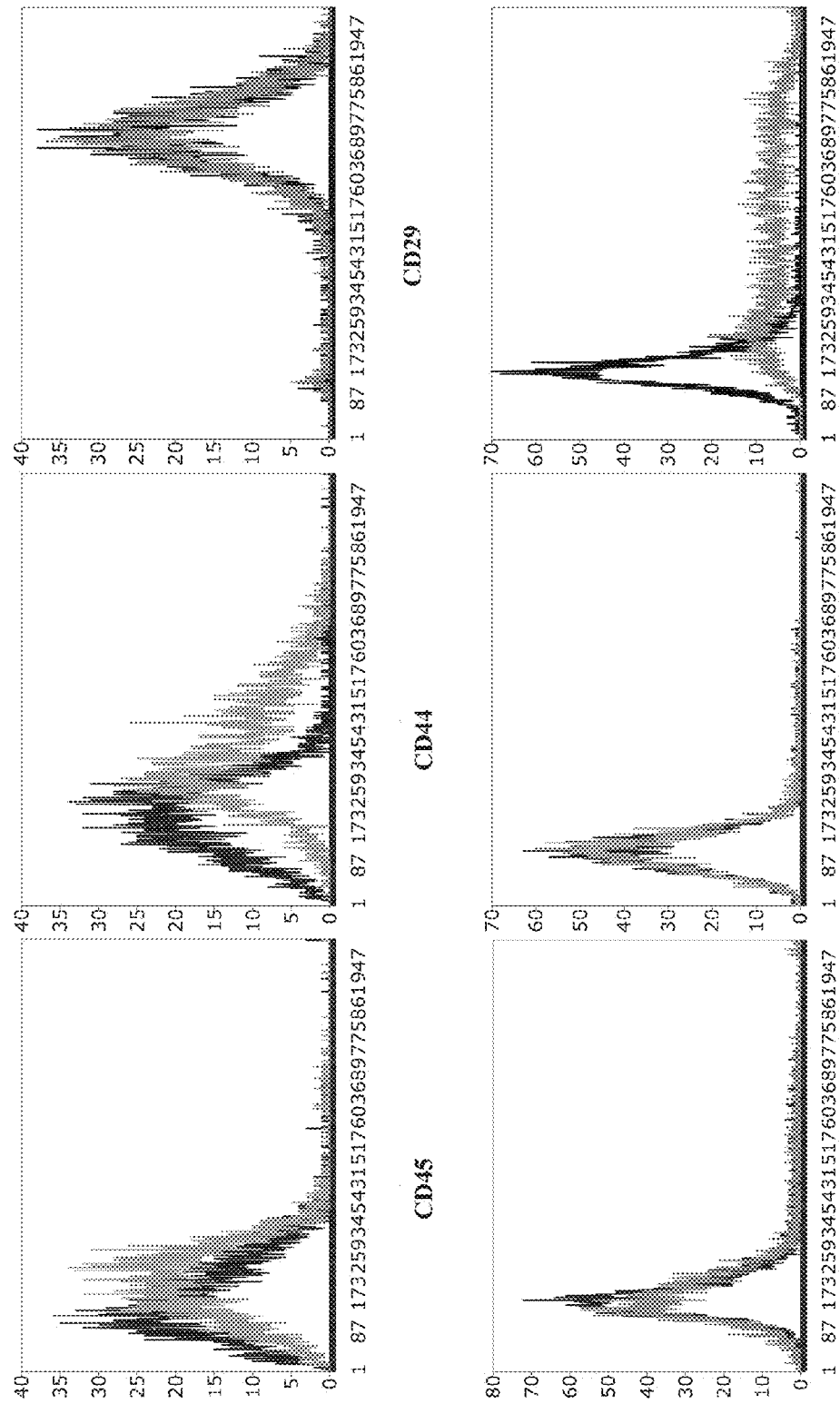

Suppression of T cells has also been observed by antigen presenting cells. To exclude the possibility that IFN-γ preferentially expanded an antigen presenting cell sub-population (found to be less than 3%) within the MSC preparation, a phenotypic analysis of the MSC following treatment with IFN-γ would show a distinct increase in the CD11b, B220 or CD45 positive population. MSC phenotype analyses were performed prior to each transplant experiment with IFN-γ-treated MSC (>10 times). No significant increases in CD45, CD11b, CD44, CD29 or B220 were noted, indicating there was no enrichment of an additional hematopoietic cell type to account for this effect [FIG. 6(B)]. In response to IFN-γ treatment, MSC increased expression of MHC class II. These findings suggest MSC phenotype and function are modified in response to IFN-γ concentration.

Example 16

In Vivo Levels

With the identification of a critical level of IFN-γ required for MSC activation, the serum of transplant recipients were analyzed to determine when such levels were observed in vivo. Serum IFN-γ was measured by ELISA in pg on days 0, 1, 2, 7, 14, 21, 30 and was converted to units (conversion factor=10 units per pg, FIG. 6(C)). No serum IFN-γ was detected on day zero (at the time of transplant) or one. A small increase on day two, 2.7±2.7 units, was followed by a dramatic increase on day seven, 7232±2340 units. By day twenty-one, levels had decreased to 207±149 units, with 63±63 units noted on day 30. These data suggest, following transplantation, circulating IFN-γ at the time of transplant are not sufficient to activate MSC. By day 30 there is also insufficient circulating IFN-γ for MSC activation, providing a possible explanation for the lack of MSC efficacy when administered on day 30. To test whether IFN-γ alone had an effect on GVHD, we retreated 3 animals with 500 units IFN-γ iv on day 0 in the absence of MSC. All three animals survived to day 50, indicating a beneficial effect of this treatment on mortality, however all three developed severe GVHD with alopecia, weight loss, and scabbing, requiring euthanasia. These data suggest that while IFN-γ has a beneficial effect on GVHD mortality, activated MSC appear to have superior efficacy, since treatment with activated MSC on day 0 prevented the development of GVHD.

Example 17

Wound Healing in Diabetic Maquaques

Animals

Healthy juvenile (aged 3 to 4 years) cynomologus maquaques of both sexes and weighing between 3-7 kg were used. The animals were housed under conditions approved by the Association for the Assessment and Accreditation of Laboratory Animal Care International. The studies were performed under protocols approved by the Animal Care Committee (ACC) of the University of Illinois at Chicago.

Experimental Design

Normal (n=1) and diabetic animals (n=3) were used for wounding experiments. Diabetic animals were used at least 60 days after streptozotocin treatment. Diabetes was assessed by measuring daily glucose levels twice and performing IVGTT after 3 weeks of STZ injection.

On animals under fentanyl (dose) and propofol (dose) anesthesia four 3×2 cm wounds were placed on skin of medial and lateral side of upper extremities. On each wound different scaffolds were placed: a) Integra alone, b) Integra with nMSCs, c) Integra with aMSCs, d) no scaffold (wet gauze).

Wounds were monitored by laser Doppler in every hour. After 6 hours biopsies were taken from the wound bed and wound edge. In n=1 normal animal CFDA-SE labeled aMSCs containing scaffold were placed on femoral wound, fluorescent cell migration after 6 hours were follow up by confocal microscopy.

Preparation of MSC Loaded Integra Scaffolds

Integra™ dermal regeneration template (Integra Life Sciences, Plainsboro, N.J.) is a bilayered membrane system consisting of a silicone top and a layer made of collagen type I and chondroitin-6-sulphate. 1 million/cm$^2$ naïve or activated MSCs were placed in 500 mcl culture media on collagen/C6S face of 3 cm×2 cm Integra scaffolds 12 hours before placement on the wounds. After 3 hours 5 ml of MSC culture media was added to the scaffold containing Petri dish. After overnight incubation culture media was replaced with DPBS.

Collection, Isolation, and Expansion of MSC

BM aspirates were obtained from the iliac crests of maquaques after ketamine (10 mg/kg i.m.) and xylazine (1 mg/kg i.m.) anesthesia. The cells were counted, and plated at a concentration of 270-300,000 cells/cm2 onto 185 cm2 Nunc Solo flasks (NuncInc., Naperville, Ill., USA). The cells were cultured in Dulbecco's modified Eagle's media-low glucose (DMEM, Life Technologies) supplemented with 10% FBS (Hyclone Laboratories, Inc., Logan, Utah, USA) and 1% penicillin-streptomycin antibiotic solution (Life Technologies). Media was replaced first at 72 hours after washing 3 times with DPBS and then every fourth day thereafter. MSCs grew as symmetric colonies until they reached 80% confluence and were subcultured at 5-7 days by treatment with 0.25% trypsin and 0.53 mM EDTA (Life Technologies) for 5 minutes, washed with serum-containing media, collected by centrifugation at 800 g for 5 minutes, and seeded into fresh flasks at 5,000-6,000 cells/cm2. Cells were cultured for up to 6 passages (about 6 weeks) using media replacement every 4 days and passage every 5 to 7 days. NPH MSCs were activated with human recombinant IFN-gamma (Peprotech Inc.) for 6 days. Before placement on scaffold, MSC were trypsinised and removed from culture flask, washed three times in DPBS and 6 million MSCs for each scaffold were resuspended in 500 microliter DPBS.

Phenotypic and Functional Characterization of MSC

The cells were harvested from the tissue culture flasks by treatment with 0.25% trypsin and 0.53 mM-EDTA and PBS. Cells in solution at a concentration of 0.5×10 cells/mL were stained for 20 minutes with 10-20 uL of a panel of monoclonal antibodies that have been previously demonstrated to identify hMSC. Monoclonal antibodies to CD34 (12.8) and CD45RA (Becton-Dickinson, Mountain View, Calif., USA) were used to identify cells as hematopoietic. Labeled cells were thoroughly washed with two volumes of PBS and fixed in flow buffer (1% paraformaldehyde, 0.1% sodium azide, and 0.5% bovine serum albumin in PBS). The labeled cells were analyzed on a FACScan or FACSVantage (Becton-Dickinson) by collecting 10,000 events with the CellQuest Software Program (Becton-Dickinson).

Laser Doppler

Microvascular status was also evaluated at baseline and every hour using the Perimed PIM 2 scanner. This noninvasive device generates mean voltage values from the entire surface of the wound bed. Laser Doppler imaging (LDI) corrects for spatial variations noted in single periwound measurement devices by imaging a larger surface area and calculating average perfusion values. Two mirrors guide a He—Ne laser beam sequentially over the skin surface. At each measurement site (4096 maximum), a tissue volume of a few hundred micrometers is illuminated. A photodetector records backscattered Doppler-broadened light, which is created by the interaction of the beam with the moving blood cells. The light signal is converted into an electrical signal and transferred to a signal processor and stored in computer memory. An image matrix is created by dividing the full range of values into 6 color-coded intervals. This process results in a multicolored picture (using a color printer), which represents the microvascular perfusion in the scanned region. By converting the image matrix to an ASCII format, the data was analyzed by statistical software package.

Confocal Microscopy

In additional non diabetic animal, activated MSCs were labeled with CFSE (Vybrant Cell Tracker Kit, Invitrogen) and placed on Integra as above. After 6 hours on the wound, wound bed and wound edge biopsies were taken. OCT embedded samples were frozen on dry ice. 6 micron sections were fixed in ice-cold methanol and were mounted with 4,6-diamidino-2-phenylindole (DAPI) containing mounting medium (Ultracruz with DAPI; Santa Cruz Inc., San Diego, Calif., USA). Green fluorescent CFSE-labeled MSCs were detected with a Zeiss LSM 510 confocal microscope.

Cultures of interferon activated and naïve non-human primate MSCs were on Integra scaffold for local delivery on autologous and allogeneic diabetic wounds. The seeded activated and naïve MSCs established rapidly on the scaffold and propagated homogeneously in the matrix. Even if there was not observed proliferation rate similar to those in 2D cultures, the 3D cultured MSCs maintained a steady state population and long-term viability on the scaffolds. Cells attached to collagen fibers developed a fibroblast-like phenotypes, indicating that Integra scaffolds provided an appropriate environment for cellular growth and differentiation.

To test the clinical feasibility of the MSC loaded Integra scaffold, both naïve and activated MSCs were safely and successfully applied to non-human primate acute diabetic wounds. $10^6$ MSC/cm$^2$ MSC were applied where this cell dose via fibrin spray was established as the optimal dose for higher wound closure rates in human chronic wounds.

Immunofluorescence imaging studies of CFDA-SE labelled MSC migration showed that the cells from the applied scaffold migrated and established toward the wound bed showing their maintained function and viability. The cells were also migrated in early timepoint (4 h after Integra placement) to regional draining lymph nodes where peripheral immune system participates in the wound healing inflammatory phase. The extent of migration outside from the scaffold did not reached massive levels at the first 6 hours suggesting that primary role of the MSCs are the coordination and stimulation of the wound healing process through their paracrin release.

Diabetic hyperglycemia and the concomitant oxidative stress damage DNA, proteins, and lipids in various tissues resulting in dysfunction of cells and enzyme systems involved in wound healing. One example is the dysregulation of COX-1-coupled prostaglandin that contributes to diabetes-impaired wound healing. This same pathway is one of the main effector mechanisms of MSCs to exert their immunoregulatory effects on inducing host macrophages to produce IL-10.

In diabetic rodents and patients host MSCs has reduced proliferative/clonogenic ability, decreased capacity of adhesion and migrative mobility that can all participate as a cofactor in the inability of healing of chronic wounds. Therefore, restoring locally the intact mesenchymal stem cell pool through the Integra scaffold is crucial to achieve optimal conditions.

In a preclinical primate model, the focus in on the early environmental changes of the first inflammatory phase that in diabetes is emphasized in inflammatory signals (IFN gamma, IL 1beta), but impaired in delivering sufficient regenerative and angiogenic signals as VEGF, TGFbeta1, IGF1.

The modification achieved of the wound bed microenvironment in early inflammatory phase through the bioengineered scaffold; in activated MSC treated wounds angiogenic VEGF and early capillary blood flow was increased significantly promoting more regenerative healing process.

Interferon gamma activation of MSCs itself increases their VEGF production. The wound bed for VEGF measurements showing tissue related VEGF content that can be contributed to the release VEGF from MSCs or from migrated proangiogenic macrophages (M2) and endothelial cells as well. MSCs can promote the induction of alternatively activated macrophages that increase extracellular matrix deposition such as collagen type I, collagen type III, matrix metalloproteinase (MMP)-1, tissue inhibitor of matrix metalloproteinase (TIMP)-1 and TGF-b1 and can support also endothelial cells to participate in angiogenesis.

Applying the predicting concept of voltage increase, present results suggest that aMSC labelled scaffold treated wounds may have an ameliorated healing process respect to control scaffold treated ones.

Materials and Methods

Animals

Young and old C57BL6 mice underwent incisional wounds and were treated with either naive mesenchymal stem cells, activated mesenchymal stem cells, or vehicle to examine MSC effects on tensile strength in the aged skin. To test whether the benefits of MSC treatment could be attributed to the participation of host macrophages, liposomal clodronate was used to deplete host macrophages.

Male C57BL/6 (H-2 Kb) mice, 12 weeks old, designated as "young mice" were purchased from Charles River (Wilmington, Mass.) and aged, as required, in the facility to achieve 18 month old aged mice. All mice were housed in an AAALAC accredited animal facility in multiple cages equipped with autoclaved food and water provided ad libitum. Mice were treated under conditions approved by the Animal Care Committee at the University of Illinois at Chicago (UIC).

Healthy juvenile (aged 3 to 4 years) cynomolgus maquaques of both sexes and weighing between 3-7 kg were used. The animals were housed under conditions approved by the Association for the Assessment and Accreditation of Laboratory Animal Care International. The studies were performed under protocols approved by the Animal Care Committee (ACC) of the University of Illinois at Chicago.

Male BALB/c (H-2K$^d$) and C3H(H-2K$^k$) and female C57BL/6 (H-2K$^b$) mice were purchased from Fredericks NCI (Frederick, Md.) or Charles River (Wilmington, Mass.). Male C.129S7(B6)-Ifng$^{tm1Ts}$/J (INF-γ deficient) mice were purchased from Jackson Laboratories (Bar Harbor, Me.). All mice were housed in an AAALAC-accredited animal facility in microisolator cages equipped with autoclaved food and acidified water and were treated under conditions approved by the Animal Care Committee at the University of Illinois at Chicago (UIC).

Cell Culture

MSCs were prepared as described previously[16]. Bone marrow of the femurs and tibia of 6-8 weeks old C57BL/6 mice were flushed through a 40 pm filter (Becton Dickenson, Franklin Lakes, N.J.) into MSC media, composed of 40% alpha Modified Eagle Medium (aMEM, Invitrogen, Rockville, Md.), 40% F-12 nutrient mixture (Invitrogen), 10% fetal bovine serum (FBS, Valley Biomedical, Winchester, Va.), and 1% antibiotic-antimycotic solution (Invitrogen)). The non-adherent population of bone marrow cells, plated at a density of $20 \times 10^6$ per 9.6 cm$^2$ in MSC media at 37° C. in 5% CO2, was removed after 72 h, and, adherent cells cultured for 7 additional days prior to passaging with 0.25% Trypsin (Invitrogen). Contaminating macrophages were depleted via Miltenyi immunomagnetic selection with biotinylated antibodies to CD11b (e-Biosciences, San Diego, Calif.) and CD45 (eBiosciences) and MACS anti biotin beads (Miltenyi Biotec, Auburn, Calif.). Negative cells were cultured at a density of $1 \times 10^6$ cells per flask. A homogenous cell population, as previously reported was immediately isolated following immunodepletion and characterized by flow cytometry, demonstrating less than 3% contamination with CD45+ cells. Passage 4 cells were used for these experiments. MSC were cultured with recombinant murine interferon gamma (PeproTech, Rocky Hill, N.J.) at 500 units per ml administered every three days or left naïve, and were stained with CFDA and administered at specified doses.

Wound Healing Model

C57BL/6 mice were randomly assigned to one of four treatment groups. Following anesthesia (ketamine and xylazine), a 4 cm midline incisional wound was extended to fascia on the dorsum of the animal and treated with 100 μl of PBS containing either vehicle alone, 3T3 fibroblasts, naïve MSC, or interferon gamma activated MSC administered over a square surface area of 8 cm. Each cell preparation was administered in various doses groups with a minimum of n=6, per treatment group. Subsequent experiments which studied activated MSC focused on the dose of 50,000 cells per wound. Wound closure was performed with 3 staples. Mice were treated with Buprenorphine for post-operative analgesia. For macrophage depletion, liposomal clodronate was begun 7 days prior to wounding and administered every three days ip (0.2 ml) to the 6$^{th}$ post-operative day. Clodronate, also known as dichloromethylene diphosphonate, was used for temporary and reversible elimination of macrophages as previously reported[17]. We observed 60-80% depletion of F4/80+ macrophages when splenic suspensions were stained and analyzed by flow cytometry (data not shown) with a corresponding 70-80% decrease in phagocytic activity when compared to non-treated splenic macrophages.

Tensiometry Determination of Wound Closure Mechanics

For this study, the incisional wound plus 0.5 cm surrounding skin was excised 7 or 14 days after treatment for tensiometry and punch biopsy. Tensiometry studies were conducted using an Motorized Force and Torque Measurement testing system (Mark-10 ESM Motorized Force and Torque Measurement Test Stand ESM300, Serial #2186798). Results are reported as the force component of the stress. The representative value of the overall wound strength is derived by calculating stress/strain. Stress is the amount of force required to break the wound apart/cross-sectional area of the wound. Strain is the original length of the sample/length at breaking. The raw strain values and cross-sectional areas did not vary significantly at any time point post-wounding between wounds. Thus, the differences in the overall wound strength were primarily due to the force component of the stress value.

Statistical Analysis

Experiments were repeated at least three times; each experiment included at least two vehicle treated animals. For comparative statistics between experiments, tensile strength was converted to percent of vehicle control strength. Results are expressed as mean±SD. Student's paired t test was performed for comparison of data of paired samples, ANOVA was used for multiple group comparisons, and a Bonferroni's post-test was used to determine differences between groups. A probability (P) value of 0.05 or less was considered significant.

Conditioning

Recipient mice were age matched (10-12 weeks) for each set of experiments and were exposed to lethal radiation 24 h prior to administration of donor BM and splenocytes. Irradiation was performed at the Department of Radiation Oncology at UIC after recipients were placed in a Lucite retainer for immobilization. The retainer was placed in a water equivalent phantom (box) 30×30×14.5 cc to ensure dose homogeneity during irradiation. Radiation was delivered via two portals (left and right) using a 6MV photon beam from a Clinac 2100EX (Varian Medical Systems, Palo Alto, Calif.) linear accelerator. A total of 1000 cGy at a dose rate of 100 cGy/min was delivered to the prescription point situated in the middle of the box. Across the box the delivered dose was homogeneous within +/−10%. The dose delivered to the animal was verified using ThermoLuminiscent Dosemeters (Harshaw/Bicron, Solon, Ohio) with agreement between measured and expected dose within +/−3.0%.

Bone Marrow, MSC, and Splenocyte Preparation

Following euthanasia, the BM contents of the femurs and tibia of donor Balb/C mice were flushed through a 40 μm filter (Becton Dickenson, Franklin Lakes, N.J.) into a 50 ml tube (Corning, Corning, N.Y.) containing MSC media, (40% alpha Modified Eagle Medium (αMEM, Invitrogen, Rockville, Md.), 40% F-12 nutrient mixture (Invitrogen), 10% fetal bovine serum (FBS, Valley Biomedical, Winchester, Va.), and 1% antibiotic-antimycotic solution (Invitrogen)). Splenocytes were flushed from spleens and filtered through a 40 van filter (BD) into a 50 ml tube (Corning). BM cells and splenocytes were counted and resuspended in Hanks Balanced Salt Solution (HBSS, Invitrogen) to the appropriate dose and administered to recipient mice retro orbitally on Day 0 to irradiation in a total volume of 200 μl per recipient.

To obtain MSC, BM cells were plated at a density of $20\times10^6$ per 9.6 cm² in MSC media at 37° C. in 5% $CO_2$ as previously described. The non-adherent population was removed after 72 h and the adherent cells were washed with fresh media and cultured for 7 additional days. The resulting adherent cells were harvested by incubating with 0.25% Trypsin (Invitrogen) for 6 min at 37° C. followed by gentle scraping. Cells were then incubated with biotinylated antibodies to mouse CD11b (10 μg per ml, e-biosciences, San Diego, Calif.) and CD45 (10 ug/ml, e-biosciences) for 30 min at 4° C. Positive cells were discarded after binding with MACS anti biotin beads and cohering to a magnetic column (Miltenyi Biotec, Auburn, Calif.). Negative cells were placed back into culture in Nunclon SoLo 185 cm² flasks (Nalge Nunc International, Rochester, N.Y.) at a density of $1\times10^6$ cells per flask. A homogenous cell population was immediately following immunodepletion. The uniform phenotype was confirmed, based on the expression of CD29, CD44, and Sca1, and the absence of hematopoietic (CD45, CD14, CD11b) markers. All antibodies were purchased from ebiosciences (San Diego, Calif.). The proportion of CD45+ cells in the MSC preparations used in the various experiments never exceeded 3% CD45+ cells. Prior to transplantation, cells had been passaged from 1 to 4 times. MSC primed with IFN-γ were plated at a density of $0.116\times10^6$ per 9.6 cm² well in 6 well plates. This density is the equivalent to $1\times10^6$ per 185 cm² flask. The 4 ml of MSC media in each well was supplemented with 500 units/ml recombinant murine IFN-γ (PeproTech, Rocky Hill, N.J.). On the day of transplantation (day 0), MSC were counted and resuspended at the appropriate dose in 100 μl HBSS per recipient in a 1 ml syringe (BD). MSC were injected retro-orbitally on either Day 2, 20 or 30 post irradiation. When co administered with BM and splenocytes on Day 0, the total volume remained 200 μl.

Flow Cytometry

MSC were characterized by Flow Cytometry (Cytomics FC 500, Beckman Coulter, Miami, Fla.). Briefly, MSC were resuspended at $1\times10^6$ cells per ml in FACS buffer (PBS (Invitrogen) with 2% FBS (Valley Biomedical, Winchester, Va.) and 0.1% Sodium Azide (Sigma, St. Louis, Mo.)). Following Fc block (BD Pharmingen, San Jose, Calif.) at 1 μg/$10^6$ cells for 15 min at 4° C., cells were stained with the following PE or FITC conjugated antibodies: H2 kd (SF1-1,1, BD), I-Ad (AMS-32.1, BD), CD2 (RM2-5, BD), CD3 (17A2, BD), CD4 (GK1.5, BD), CD8a (53-6.7, ebiosciences), CD11b (M1/70, ebiosciences) CD14 (rmC5-3, BD), CD44 (IM7, ebiosciences), CD45 (30-F11, BD), B220 (RA3-6B2, BD), Sca-1 (E13-161.7, BD), c-Kit (2B8, ebiosciences), Thy-1 (30-H12, BD), IFN-γ beta receptor (Abcam, Cambridge, Mass.) and appropriate isotype controls (ebiosciences or Abcam). Cells were also stained with a primary purified anti CD29 antibody (BD) at a concentration of 1 μg/$10^6$ cells, washed with FACS buffer, and then stained with a secondary PE f(ab')$_2$ fragment donkey anti rat IgG (Jackson ImmunoResearch, West Grove, Pa.) at 0.5 μg/$10^6$ cells. Flow analysis was performed following the acquisition of 10,000 events. MSC purity was verified within 2 days of transplantation. MSC were stained with FITC conjugated CD11b and CD45 as above.

GVHD Scoring

Mice were weighed twice weekly and monitored daily for survival and clinical evidence of GVHD (ruffled fur, cachexia, alopecia, and diarrhea). Control mice receiving no MSC and recipients of either $10^5$ or $5\times10^5$ MSC administered on day 2 were euthanized on day 20 for histological examination. Liver, lung, colon, spleen, and skin were excised, sectioned, stained with hematoxylin and eosin, and examined and scored by two independent pathologists blinded to treatment groups. GVHD was scored on a scale from 0 (none) to 4.0 based on the scales reported by Ferrara (skin), Grass (liver, spleen), and Hill (colon). The scales for each tissue are defined as follows: for lung 0=normal, 0.5=minimal perivascular cuffing, 1.0=perivascular cuffing, 1 to 2 cells in thickness, involving up to 15% of vessels, 1.5=perivascular cuffing, 1 to 2 cells in thickness, involving up to 15% of vessels and infiltration into parenchyma proper, 2.0=perivascular cuffing, 2 to 3 cells in thickness, involving up to 15% of vessels and infiltration into parenchyma proper, 2.5=perivascular cuffing, 2 to 3 cells in thickness, involving 25% to 50% of vessels and infiltration into parenchyma proper, 3.0=perivascular cuffing, 4 to 5 cells in thickness, involving 25% to 50% of vessels, and infiltration into parenchyma proper, 3.5=perivascular cuffing, 6 to 7 cells in thickness, involving greater than 50% of vessels, peribronchiolar cuffing (4 to 5 cells), and infiltration into parenchyma proper with severe disruption of structure, 4.0=perivascular cuffing, 6 to 7 cells in thickness, involving greater than 50% of vessels, peribronchiolar cuffing (>6 cells), and infiltration into parenchyma proper with severe disruption of structure; for colon 0=normal, 0.5=occasional necrotic crypt cell, minimal infiltration in lamina propria and submucosa (colon), 1.0=necrotic cells in up to 15% of crypts, minor infiltration of up to 20% of lamina propria (1 to 2 cell thickness in intermucosal areas and submucosa, 1.5=necrotic cells in up to 15% of crypts, minor infiltration of less than or equal to one third of the lamina propria (1 to 2 cell thickness in intermucosal areas and submucosa), 2.0=necrotic cells in ≤5% of crypts, infiltration of less than or equal to one third of the lamina propria (3 cell thickness in intermucosal areas and submucosa), 2.5=necrotic cells in 25% to 50% of crypts, infiltration of less than or equal to one third of lamina propria (3 to 4 cell thickness in intermucosal areas and submucosa), 3.0=necrotic cells in greater than 50% of crypts, infiltration of lamina propria (5 to 6 cell thickness in intermucosal areas and submucosa) with loss of ≤25% of goblet cells, 3.5=necrotic cells in greater than 50% of crypts, infiltration of lamina propria resulting in displacement of 50% of mucosa with loss of 50% of goblet cells, 4.0=necrotic cells in greater than 50% of crypts, infiltration of lamina propria resulting in displacement of greater than 50% of mucosa with loss of 75% to 100% of goblet cells; for spleen 0=normal, 1.0=necrotic/apoptotic cells, up to 10 cells/mm2 of tissue, 1.5=necrotic/apoptotic cells, up to 10 cells/mm2 of tissue and occasional hemolysis, 2.0=necrotic/apoptotic cells, ≤20 cells/mm2 of tissue, and occasional hemolysis with abnormal architecture, 2.5=necrotic/apoptotic cells, ≤0 cells/mm2 of tissue, and hemolysis in ≤25% of the tissue with abnormal architecture, 3.0=necrotic/apoptotic cells, ≤40 cells/mm2 of tissue, hemolysis in 25% to 50% of tissue with abnormal architecture and areas of leukopenia involving ≤25% of tissue, formation of fibrous bands, 3.5=necrotic/apoptotic cells, up to 40 cells/mm2 of tissue, hemolysis evident in greater than 50% of tissue with abnormal architecture and areas of leukopenia involving 25% to 50% of tissue, formation of fibrous bands, 4.0=large areas of necrosis and hemolysis evident in greater than 50% of tissue with abnormal architecture and large areas of leukopenia involving greater than 50% of tissue; for skin 0=normal, 1.0=Basal keratinocyte ballooning, 2.0=sebaceous and adnexal infiltrate, 3.0=Loss of epidermis.

Quantification of Serum IFN-γ

Twenty B6 recipients underwent irradiation followed Balb/c bone marrow transplant with accessory splenocytes as described above. Three to five recipients underwent serum sampling for each timepoint, on days 0, 1, 2, 7, 14, 20, and 30. Sera was cryopreserved and batch analyzed using Quantikine Mouse IFN-γ Immunoassay by R&D Systems (Minneapolis, Minn., Cat#: MIFOO) as per manufacturer's instructions (A Multiskan).

Ascent (Labsystems) plate reader provided OD read at 450 nm with 540 nm wavelength correction. Data were expressed as means with standard deviations.

Statistical Analyses

Treatment group sizes were designed based on an alpha of 0.05 and a power of 0.80. Each experiment was repeated at least 3 times with a minimum of n=10 per group, unless otherwise stated. Kaplan Meier curves (log rank test) were used to compare survival between treatment groups. ANOVA was used to compare GVHD scoring between groups. In all statistical analyses, a p value of 0.05 was deemed significant.

Experimental Design

Normal (n=1) and diabetic animals (n=3) were used for wounding experiments. Diabetic animals were used at least 60 days after streptozotocin treatment (ref). Diabetes was assessed by measuring daily glucose levels twice and performing IVGTT after 3 weeks of STZ injection.

On animals under fentanyl (dose) and propofol (dose) anesthesia four 3×2 cm wounds were placed on skin of medial and lateral side of upper extremities. On each wound different scaffold were placed: a) Integra alone, b) Integra with nMSCs, c) Integra with aMSCs, d) no scaffold (wet gauze).

Wounds were monitored by laser Doppler in every hour. After 6 hours biopsies were taken from the wound bed and wound edge. In n=1 normal animal CFDA-SE labeled aMSCs containing scaffold were placed on femoral wound, fluorescent cell migration after 6 hours were follow up by confocal microscopy.

Preparation of MSC Loaded Integra Scaffolds

Integra™ dermal regeneration template (Integra Life Sciences, Plainsboro, N.J.) is a bilayered membrane system consisting of a silicone top and a layer made of collagen type I and chondroitin-6-sulphate. 1 million/cm2 naïve or activated MSCs were placed in 500 mcl culture media on collagen/C6S face of 3 cm×2 cm Integra scaffolds 12 hours before placement on the wounds. After 3 hours 5 ml of MSC culture media was added to the scaffold containing Petri dish. After overnight incubation culture media was replaced with DPBS.

Collection, Isolation, and Expansion of MSC

BM aspirates were obtained from the iliac crests of maquaques after ketamine (10 mg/kg i.m.) and xylazine (1 mg/kg i.m.) anesthesia. The cells were counted, and plated at a concentration of 270-300,000 cells/cm2 onto 185 cm2 Nunc Solo flasks (NuncInc., Naperville, Ill., USA). The cells were cultured in Dulbecco's modified Eagle's media-low glucose (DMEM, Life Technologies) supplemented with 10% FBS (Hyclone Laboratories, Inc., Logan, Utah, USA) and 1% penicillin-streptomycin antibiotic solution (Life Technologies). Media was replaced first at 72 hours after washing 3 times with DPBS and then every fourth day thereafter. MSCs grew as symmetric colonies until they reached 80% confluence and were subcultured at 5-7 days by treatment with 0.25% trypsin and 0.53 mM EDTA (Life Technologies) for 5 minutes, washed with serum-containing media, collected by centrifugation at 800 g for 5 minutes, and seeded into fresh flasks at 5,000-6,000 cells/cm2. Cells were cultured for up to 6 passages (about 6 weeks) using media replacement every 4 days and passage every 5 to 7 days. NPH MSCs were activated with human recombinant IFN-gamma (Peprotech Inc, do we want dosage?) for 6 days. Before placement on scaffold, MSC were trypsinised and removed from culture flask, washed three times in DPBS and 6 million MSCs for each scaffold were resuspended in 500 microliter DPBS.

Phenotypic and Functional Characterization of MSC

The cells were harvested from the tissue culture flasks by treatment with 0.25% trypsin and 0.53 mM-EDTA and PBS. Cells in solution at a concentration of 0.5×10 cells/mL were stained for 20 minutes with 10-20 uL of a panel of monoclonal antibodies that have been previously demonstrated to identify hMSC. Monoclonal antibodies to CD34 (12.8) and CD45RA (Becton-Dickinson, Mountain View, Calif., USA) were used to identify cells as hematopoietic. Labeled cells were thoroughly washed with two volumes of PBS and fixed in flow buffer (1% paraformaldehyde, 0.1% sodium azide, and 0.5% bovine serum albumin in PBS). The labeled cells were analyzed on a FACScan or FACSVantage (Becton-Dickinson) by collecting 10,000 events with the CellQuest Software Program (Becton-Dickinson).

Laser Doppler

Microvascular status was also evaluated at baseline and every hour using the Perimed PIM 2 scanner. This noninvasive device generates mean voltage values from the entire surface of the wound bed. Laser Doppler imaging (LDI) corrects for spatial variations noted in single periwound measurement devices by imaging a larger surface area and calculating average perfusion values. Two mirrors guide a He—Ne laser beam sequentially over the skin surface. At each measurement site (4096 maximum), a tissue volume of a few hundred micrometers is illuminated. A photodetector records backscattered Doppler-broadened light, which is created by the interaction of the beam with the moving blood cells. The light signal is converted into an electrical signal and transferred to a signal processor and stored in computer memory. An image matrix is created by dividing the full range of values into 6 color-coded intervals. This process results in a multi-colored picture (using a color printer), which represents the microvascular perfusion in the scanned region. By converting the image matrix to an ASCII format, the data was analyzed by statistical software package.

Confocal Microscopy

In additional non diabetic animal, activated MSCs were labeled with CFSE (Vybrant Cell Tracker Kit, Invitrogen) and placed on Integra as above. After 6 hours on the wound, wound bed and wound edge biopsies were taken. OCT embedded samples were frozen on dry ice. 6 micron sections were fixed in ice-cold methanol and were mounted with 4,6-diamidino-2-phenylindole (DAPI) containing mounting medium (Ultracruz with DAPI; Santa Cruz Inc., San Diego, Calif., USA). Green fluorescent CFSE-labeled MSCs were detected with a Zeiss LSM 510 confocal microscope.

The invention claimed is:

1. A method to improve wound healing in a mammal, the method comprising:
   (a) activating mammalian mesenchymal stem cells from bone marrow with IFN-γ; and
   (b) administering the activated mammalian stem cells to the mammal in need thereof in an amount effective to increase tensile wound strength compared to a control mammal receiving naïve mammalian stem cells or vehicle controls.

2. The method of claim 1 wherein wound healing is enhanced by recruiting macrophages to the wound site.

3. The method of claim 1, wherein the activating is by a high dose of interferon gamma/ml.

4. The method of claim 3 wherein the high dose is greater than 50 units interferon gamma/ml.

5. The method of claim 4 wherein the high dose is about 2,000 or up to 20,000 for 2 hour units.

6. The method of claim 1, wherein the bone marrow is human bone marrow.

7. The method of claim 3 wherein activating is achieved by at least 2 successive pulses of exposure to >50 units/ml IFN-γ.

8. The method of claim 3 wherein high doses are 500 units for 6 days.

9. The method of claim 1, wherein administering is approximately at the time of, or after, the wound occurs.

10. The method of claim 1, wherein tensile strength is restored to levels of younger mammals.

11. The method of claim 3, wherein the dose of activated MSC per wound is lower than required for non-activated MSC's to achieve equivalent tensile strength.

* * * * *